United States Patent [19]

Reinert et al.

[11] Patent Number: 4,657,554
[45] Date of Patent: Apr. 14, 1987

[54] WATER-SOLUBLE AZAPHTHALOCYANINES AND THEIR USE AS PHOTOACTIVATORS IN BLEACHING

[75] Inventors: Gerhard Reinert, Allschwil; Gerd Hölzle, Liestal; Gregor Graf, Basel, all of Switzerland

[73] Assignee: Ciba-Geigy Corporation, Ardsley, N.Y.

[21] Appl. No.: 736,913

[22] Filed: May 22, 1985

[30] Foreign Application Priority Data

May 28, 1984 [CH] Switzerland ............ 2609/84

[51] Int. Cl.[4] ............... A01N 55/02; C07D 487/22; C09B 47/04; D06L 3/02
[52] U.S. Cl. .......................... 8/107; 8/101; 8/102; 8/103; 540/121; 540/122; 540/123; 540/140
[58] Field of Search .............. 8/107, 101, 103, 102

[56] References Cited

U.S. PATENT DOCUMENTS

| | | | |
|---|---|---|---|
| 3,094,534 | 6/1963 | Griot et al. | 548/452 |
| 3,094,535 | 6/1963 | Kenney et al. | 260/245.74 |
| 3,923,645 | 12/1975 | Anderson et al. | 568/26 |
| 3,927,967 | 12/1975 | Speakman | 8/103 |
| 4,033,718 | 7/1977 | Holcombe et al. | 8/103 |
| 4,077,768 | 3/1978 | Johnston et al. | 8/107 |
| 4,094,806 | 6/1978 | Wiers | 8/103 |
| 4,166,718 | 9/1979 | Reinert et al. | 8/111 |
| 4,240,920 | 12/1980 | de Luque | 252/99 |
| 4,255,273 | 3/1981 | Sakkab | 252/99 |
| 4,256,597 | 3/1981 | Sakkab | 252/99 |
| 4,318,883 | 3/1982 | Polony et al. | 422/22 |
| 4,368,053 | 1/1983 | Eckhardt et al. | 8/102 |
| 4,394,125 | 7/1983 | Holzle et al. | 8/103 |
| 4,400,173 | 8/1983 | Beavaw | 8/107 |
| 4,456,452 | 6/1984 | Holzle et al. | 8/103 |
| 4,497,741 | 2/1985 | Holzle et al. | 8/101 |
| 4,540,518 | 9/1985 | Eckhardt et al. | 260/242.2 |
| 4,566,874 | 1/1986 | Holzle et al. | 8/103 |

FOREIGN PATENT DOCUMENTS

| | | |
|---|---|---|
| 0003149 | 7/1979 | European Pat. Off. . |
| 0003371 | 8/1979 | European Pat. Off. . |
| 0003861 | 9/1979 | European Pat. Off. . |
| 0054992 | 6/1982 | European Pat. Off. . |
| 1372035 | 10/1974 | United Kingdom . |
| 1408144 | 10/1975 | United Kingdom . |

*Primary Examiner*—A. Lionel Clingman
*Attorney, Agent, or Firm*—Edward McC. Roberts; Irving M. Fishman

[57] ABSTRACT

Novel azaphthalocyanines are described which are of the formula

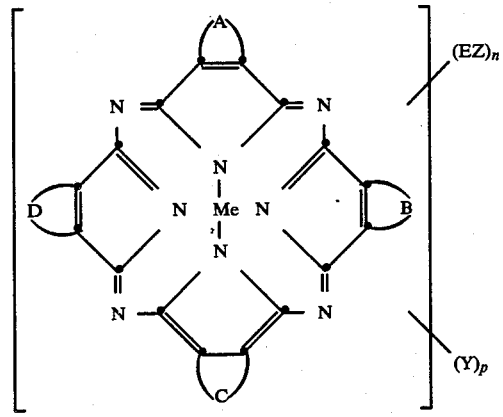

in which Me is Al(III), Zn(II), Ge(IV) or Sn(IV), E is an anionic group, Z is a cation, Y is a halogen, n is any desired number from 1 to 3 and p is any desired number from 0 to 2, the sum n+p being at most 8 and A, B, C and D independently of one another completing a benzene ring or a ring of the formula

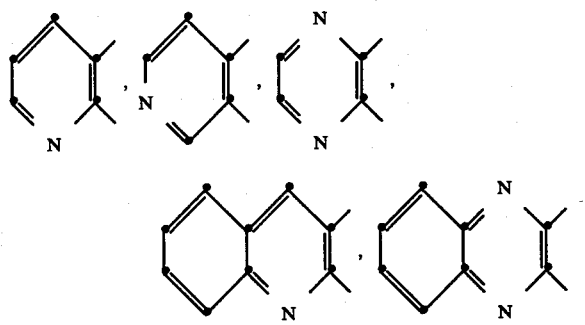

at least one of the rings completed by A, B, C or D being one of the said heterocyclic rings.

The novel compounds can be used as photoactivators, in particular for bleaching textiles and for controlling microorganisms in or on organic or inorganic substrates.

Bleaching, washing and steeping agents and antimicrobially active agents are also described which contain the novel azaphthalocyanine compounds. The azaphthalocyanine pigments which arise as intermediates and which do not carry groups EZ imparting solubility in water, their preparation and their use as photosensitizers in non-aqueous or heterogeneous systems are likewise described.

4 Claims, No Drawings

WATER-SOLUBLE AZAPHTHALOCYANINES AND THEIR USE AS PHOTOACTIVATORS IN BLEACHING

The present invention relates to novel, water-soluble azaphthalocyanines, processes for their preparation, their use as photoactivators (photosensitisers) or singlet oxygen producers, in particular for bleaching or removing spots from textiles and for controlling microorganisms in or on organic or inorganic substrates, and to bleaching agents, washing agents, rinsing agents and steeping agents and to antimicrobial agents containing the novel azaphthalocyanine compounds, and also to novel water-insoluble azaphthalocyanines appearing as intermediates, and to processes for the preparation thereof.

It is known that various water-soluble phthalocyanine compounds, in particular those having zinc and aluminium as the central atom, have a photosensitising action and can therefore be used as photobleaching agents or antimicrobial active compounds. In this context, see, inter alia, U.S. Pat. Nos. 3,927,967, 4,033,718, 4,166,718 and 4,094,806; DE-A Nos. 2,222,829, 2,627,449 and 2,812,261; EP-A Nos. 3,149, 3,371, 3,861, 26,744, 35,470, 47,716, 54,992 and 81,462. The publications mentioned also describe agents containing the said water-soluble phthalocyanine compounds.

The novel water-soluble azaphthalocyanines according to the present invention are of the general formula

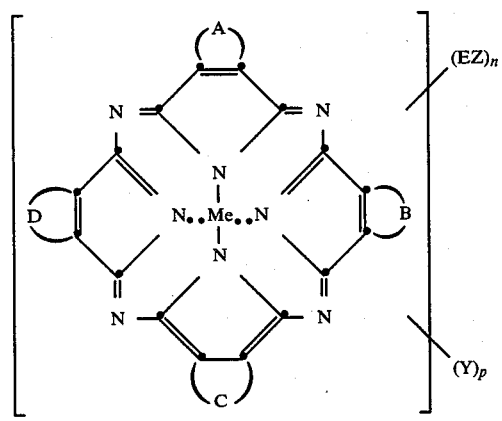

(1)

in which Me is Al(III), Zn(II), Ge(IV) or Sn(IV), E is a sulfo, carboxyl, phosphate, sulfate, sulfinyl, disulfimide or sulfocyanimide group or a radical containing one or more of the abovementioned groups, Z is a cation, Y is a halogen, n is any desired number from 1 to 3 and p is any desired number from 0 to 2, the sum n+p being at most 8 and A, B, C and D independently of one another completing a benzene ring or a ring of the formula

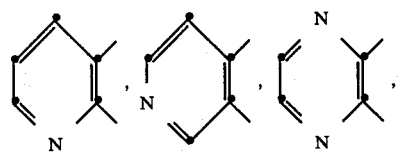

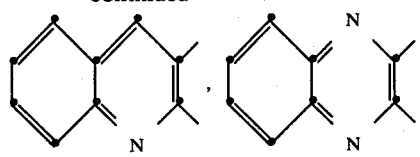

at least one of the rings completed by A, B, C or D being one of the heterocyclic rings shown.

The number of nitrogen-containing heterocyclic rings fused to the tetraazoporphine skeleton is thus 1 to 4. The number of the fused benzene rings thus is 3 to 0.

Those compounds of the formula (1) are particularly preferred in which one or two of the rings completed by A, B, C and D are of the formula

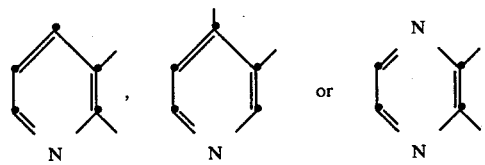

and the other (3 or 2) rings are benzene rings.

The groups E which impart water-solubility are bonded to the rings A, B, C and/or D or to rings fused to them. As is known from phthalocyanine chemistry, it is difficult to establish the precise position of the substituents. The substituted phthalocyanines, as also the azophthalocyanines according to the invention, frequently do not represent single substances, but mixtures. The number of substituents (degree of substitution) present in the molecule is therefore rarely an integer (n or p not an integer). It is also to be noted that the individual substituents E or Y can be identical or different in each case, i.e. entirely different substituents imparting solubility in water or neutral substituents can also be present in one molecule.

Z is any desired cation opposite an anionic group E. If a group E contains several anionic radicals, Z can have the same valency as the group E or a corresponding number of monovalent counter-ions Z can be present. The following are examples of cations Z: the hydrogen ion, alkali metal and alkaline earth metal ions and unsubstituted and substituted ammonium ions. Substituted ammonium ions are derived, for example, from primary, secondary or tertiary aliphatic or cyclic amines. Examples of these ions are ammonium ions of the formula

in which R', R" and R''' independently of one another are hydrogen or alkyl (preferably having 1-4 C atoms) which is unsubstituted or substituted by halogen, hydroxyl, phenyl or cyano, at least one R substituent being other than hydrogen. Two R radicals together can also form the groups needed to complete a saturated 5-membered or 6-membered nitrogenheterocyclic structure, and this can, if desired, also contain an additional oxygen or nitrogen atom as a member of the ring. The following are examples of heterocyclic structures of this type: piperidine, piperazine, morpholine, pyrrolidine, imidazoline and the like.

Preferred cationic counter-ions are the hydrogen ion, alkali metal ions (particularly $Na^+$ and $K^+$) and substituted and unsubstituted ammonium ions.

The anionic groups E imparting solubility in water are preferably sulfo, carboxyl, phosphate, sulfate, sulfinyl, disulfimide and sulfocyanimide groups or one or more radicals containing the above groups. Particularly suitable groups E are of the formulae

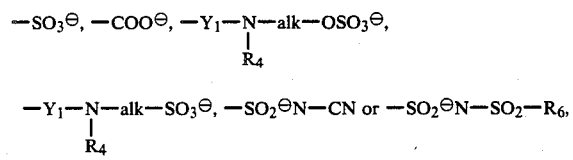

in which $R_4$ is substituted or unsubstituted alkyl or hydrogen, $R_6$ is substituted or unsubstituted alkyl, substituted or unsubstituted phenyl or naphthyl, alk is substituted or unsubstituted alkylene and $Y_1$ is $-SO_2-$ or $-CO-$, preferably $-SO_2-$, $-SO_3^\ominus$, $-COO^\ominus$, $-SO_2-N^\ominus-CN$ and $-SO_2-N^\ominus-SO_2-R_6$, in which $R_6$ is alkyl having 1 to 4 carbon atoms, being of particular importance.

Preferred compounds of the formula (1) contain those groups EZ, in which E is $-SO_3^\ominus$ and Z is a hydrogen ion, alkali metal ion or a substituted or unsubstituted ammonium ion, in particular a hydrogen, sodium or ammonium ion.

Y is a neutral substituent which does not impart solubility in water and is halogen, in particular chlorine, bromine or iodine.

In formula (1), n is preferably any desired number from 1 to 3, and p is any desired number from 0 to 2. The number of substituents imparting solubility in water, which must be present as a minimum in the molecule, also deoends on the number of substituents Y present. Regardless of whether groups which do not impart solubility in water are or are not present (p=0), sufficient groups imparting solubility in water must be present in the molecule in every case to ensure an adequate solubility in water. A minimum solubility of only 0.001 g/l can be sufficient, and in general a minimum solubility of 0.1 to 20 g/l is advantageous.

The indices n and p (provided that p is not zero anyway) can be any desired numbers within the range indicated. As is customary in phthalocyanine chemistry, the individual products frequently consist of mixtures, since products which are not single substances are often formed in the course of preparation (for example sulfonation, sulfochlorination, halogenation and the like). The indices therefore represent the "degree of substitution", which does not, of course, have to be integral.

The azaphthalocyanines according to the invention contain the central atom Me. However, Me can also be a grouping consisting of a central atom and one or more ligands, since it is generally known from phthalocyanine chemistry that, in the case of central atoms having valences above 2, the free valencies are saturated by one or more additional ligands. These additional ligands can, for example, be anions. These anions may, for instance, be identical with the anions of the particular metal compounds which were used for the preparation of the complex. Examples of such anions are halide, sulfate, nitrate, phosphate and hydroxyl ions, ions of organic carboxylic acids (for example the acetate or formate ion) or sulfonic acids (for example the tosyl anion). Some higher-valent central atoms can also be present as oxo-ions, for example $ZrO^{2+}$, $TiO^{2+}$, $CrO_2^{2+}$ and the like. All these groupings are to be understood as covered by the term "central atom".

The preferred central atoms are Zn(II), Al(III), Sn(IV) and Ge(IV), especially Zn(II) and Al(III).

Azaphthalocyanines according to the invention of particular importance in practice are of the formula

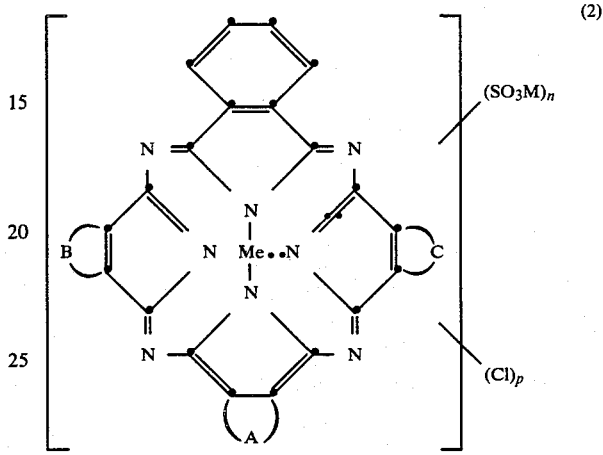

in which B represents the complement to form 2,3- or 3,4-pyridino or 2,3-pyrazino, A and/or C represent the complement to form benzo and, in the case of "or", one of these two symbols represents the complement to form 2,3- or 3,4-pyridino or 2,3-pyrazino, M is hydrogen, sodium, potassium or ammonium and Me is Zn(II), Al(III) or Ge(IV), and n and p are as defined above.

In a particularly preferred group of compounds of the formula (1), Me is Al(III), Zn(II) or Ge(IV), EZ is $-SO_3Na$, n is any desired number from 1 to 3 and p is 0, and A, B, C and D independently of one another complete a benzene ring or a 2,3- or 3,4-pyridine ring.

The compounds, according to the invention, of the formula (1) can be prepared by processes which are known per se and are customary in phthalocyanine chemistry. In this respect, it is possible essentially to employ three different methods:

(A) The central atom is introduced into a metal-free (i.e. containing no central atom Me) azaphthalocyanine (compound of the formula (1) without Me) which contains the substituents EZ and, if appropriate, Y by reaction with a suitable metal compound (for example a salt) of the central atom. (B) The substituents imparting solubility in water are introduced into the appropriate azaphthalocyanines with a central atom (azaphthalocyanine pigments) by means of suitable reactions.

(C) The substituents imparting solubility in water are already present in the starting materials (for example phthalic anhydride, phthalodinitrile and the corresponding naphthalenedicarboxylic acid derivatives, for example dicarboxylic acid derivatives of the nitrogen-containing heterocyclic structures A to D) required for the synthesis of the azaphthalocyanine ring system. The synthesis of the ring system and the incorporation of the central atom are then effected by customary processes, either simultaneously or successively.

Depending on their nature, the substituents which do not impart solubility in water can also already be present in the starting materials, or they can be introduced into the synthesised ring system subsequently, for example by halogenation, either before or after the incorporation of the central atom. In some processes for the preparation of the azaphthalocyanine ring system, such substituents (for example chlorine) are also introduced directly, for example by using chlorides as catalysts and as salts of the central atom to be incorporated.

If the above process (A) is used, the appropriately substituted azaphthalocyanines without a central atom can, for example, be reacted with a compound of the appropriate central atom, for example with a salt thereof or with an alcoholate, if the central atom is a metal which forms alcoholates. Examples of solvents suitable for this reaction are mixtures of water and organic solvents, for instance tertiary amines, or anhydrous solvents, for example pyridine and chlorobenzenes. Resulting metal complexes can, of course, also be converted into other metal complexes. Process variant (A) is, for example, also described in U.S. Pat. No. 4,318,883.

The methods of introducing substituents into the ring system (alternative B) above) are very numerous and vary depending on the nature of the substitution. Only a few examples of such methods will be given below:

The introduction of sulfonic acid groups ($E=SO_3^-$) can be effected for example, by sulfonation, for instance by means of oleum. Alternatively, appropriate non-sulfonated phthalocyanines can also be reacted with chlorosulfonic acid to give the corresponding phthalocyanine sulfochlorides and the latter can then be hydrolysed to the sulfonic acids. In both cases, the free sulfonic acid groups can subsequently be converted into their salts. Methods of sulfonation of this type are described, for example, in U.S. Pat. No. 4,318,883 and in EP-A No. 47,716.

Carboxyl groups can be introduced into the unsubstituted azaphthalocyanines by reacting the latter with phosgene and aluminium chloride and hydrolysing the resulting acid chloride, or by reaction with trichloroacetic acid. The acid chlorides can also be converted into other water-soluble carboxylic acid derivatives in a known manner.

The compounds of the formula (1) which are substituted by sulfonamide or carboxamide groups of the type shown in the following formulae $-Y_1-N(R_4)-alk-OSO_3^\ominus$ and $-Y_1-N(R_4)-alk-SO_3^\ominus$ are obtained from the above-described $SO_2Cl$-substituted or $COCl$-substituted, respectively, azaphthalocyanines (obtained by reaction with chlorosulfonic acid or with phosgene and $AlCl_3$) by reaction with correspondingly substituted aliphatic or aromatic amines.

Compounds of the formula (1), in which E is a group of the formula $-SO_2^\ominus N-CN$ or $-SO_2^\ominus N-SO_2-R_6$, are prepared, for example, by reacting the corresponding azaphthalocyanine with chlorosulfonic acid and further reacting the resulting sulfochloride with cyanamide or with ammonia and a halide of the formula $Hal-SO_2-R_6$ (Hal=halogen, in particular chlorine) or with hydrazine or a hydrazine derivative. The relevant processes are described, for example, in EP-A No. 81,462 for the case of non-heterocyclic phthalocyanines.

Preferred azaphthalocyanines of the formula (1), in which E is a group of the formula

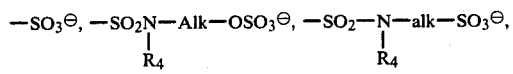

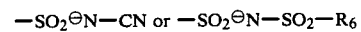

can be prepared, for example, by reacting an azaphthalocyanine of the formula

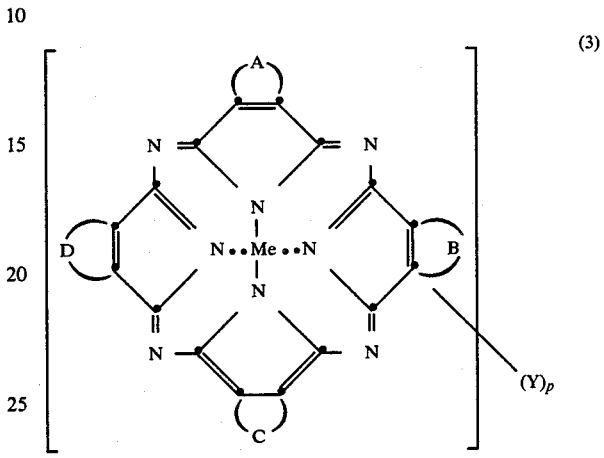

(3)

in which the general symbols are as defined in formula (1), with chlorosulfonic acid to give an azaphthalocyanine of the formula

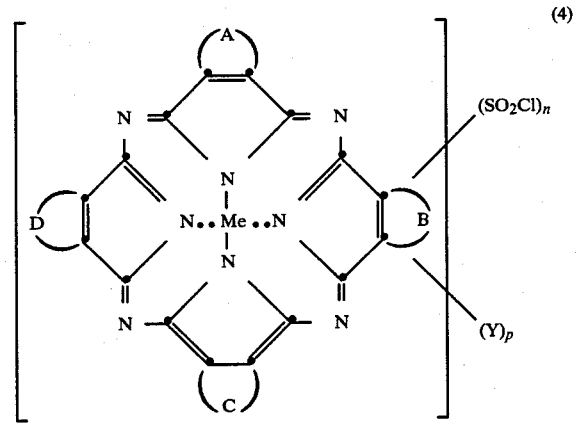

(4)

and (a) hydrolysing the latter for the preparation of compounds with $E=-SO_3^\ominus$, (b) reacting it with a amine of the formula

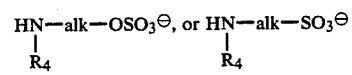

for the preparation of compounds with substituents which contain the grouping

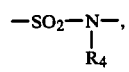

(c) reacting it with cyanimide or a salt thereof for the preparation of compounds with $E=SO_2-N-CN$, or (d) first reacting it with ammonia and then reacting the resulting sulfonamide with a halide of the formula hal—SO$_2$—R$_6$, hal being a halogen atom, in particular chlorine, for the preparation of compounds with E=—SO$_2$⊖N—SO$_2$—R$_6$.

Variant (a) is preferred for the preparation of compounds of the formula (1), which contain sulfo groups. Such sulfo-substituted azophthalocyanines of the formula (1) (E=SO$_3$⊖) can also be prepared by sulfonating an azophthalocyanine of the formula

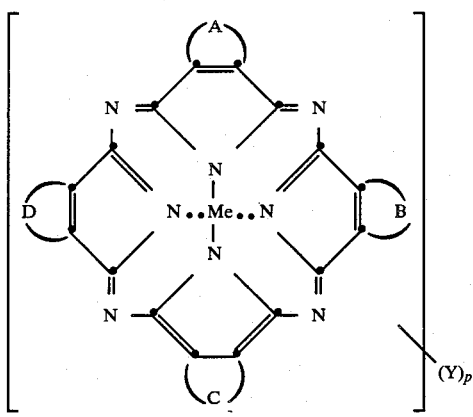

(3)

with oleum.

Preferred reaction conditions for the above variant (a) (sulfochlorination and subsequent hydrolysis) and for the sulfonation with oleum are described, for example, in U.S. Pat. No. 4,318,883 and EP-A No. 47,716. Regarding preferred reaction conditions for the above variants (c) and (d), see, for example, EP-A No. 81,462.

The compounds, according to the invention, of the formula (1) have excellent photosensitising properties and are outstanding producers of singlet oxygen. They can, therefore, be used in accordance with the invention as photosensitisers, photoactivators (these two terms are frequently used synonymously in the literature) and/or singlet oxygen producers. The fields in which they can be used are very diverse. The compounds of the formula (1) can be employed in all cases where reactions with singlet oxygen are intended to take place.

These can, for example, be photocatalysed reactions in organic chemistry and also in polymer chemistry. Surprisingly, in some respects the compounds according to the invention have better or more advantageous properties than known photoactivators.

However, the compounds according to the invention are preferably used as photodynamically active agents (i.e. as agents which, under the action of light, are effective especially against microorganisms) and, in particular, as photobleaching agents. They are therefore used, for example, for bleaching or removing spots from textiles and for controlling microorganisms in or on organic or inorganic substrates or for protecting the latter against attack by microorganisms, especially as bleaching agents or antimicrobial active substances in detergents and washing liquors, and also as disinfectants for laundry, solid surfaces, swimming pools and effluents from sewage treatment plants.

The present invention also relates to a process for carrying out a photosensitised (photoactivated) reaction or a reaction with singlet oxygen, wherein one or more azaphthalocyanines of the formula (1) are brought into contact with a substrate, in which or on which the said reaction is to take place, in the presence of oxygen and water, and are irradiated with light.

In particular, the present invention relates to a process for bleaching or removing spots from textiles and for controlling microorganisms in or on organic or inorganic substrates or for protecting the latter against attack by microorganisms, wherein the textiles or the substrates to be freed from or protected against microorganisms are treated with azaphthalocyanines defined in formula (1) in the presence of water and while being irradiated with light.

In order to develop their antimicrobial activity, the azaphthalocyanine compounds according to the invention require the presence of oxygen and water as well as irradiation with light. Treatment is therefore generally carried out in aqueous solutions or on moist substrates, and the source of oxygen used is the oxygen dissolved in the water or atmospheric oxygen.

The irradiation can be effected by means of an artificial source of light or by means of sunlight. A good effect is achieved, for example, by means of light within the range between about 300 and 2,500 nm. Thus, irradiation can be carried out, for example, using a commercially available incandescent lamp. The intensity of illumination can vary within wide limits. It depends on the concentration of active substance, on the nature of the substrate or on the substances additionally present which influence the light yield. A further parameter which can be varied is the exposure time, i.e. for the same effect exposure must be longer at a lower light intensity than at a higher intensity. In general, depending on the field of use, exposure times of a few minutes up to a few hours are possible.

If the process is carried out in an aqueous liquor (for example sterilisation of textiles), the irradiation with light can either be carried out directly in the treatment liquor by means of an artifical source of light mounted inside or outside the liquor, or the substrates, in a moist state, can subsequently either be irradiated, again by means of an artificial source of light, or can be exposed to sunlight.

Good antimicrobial effects can be achieved even with very low concentrations of active substance, for example at 0.001 ppm. Depending on the field of use and on the azaphthalocyanine derivative employed, a concentration between 0.005 and 100, preferably 0.01 and 50, ppm is preferable. Since the active substances are dyes, the upper limit of concentration is given by the fact that an undesirable colouration of the substrates would be observable if it were exceeded. The upper limit of concentration is thus limited by the strength of the intrinsic colour of the agents employed, but it can be 1000 ppm or more.

The azaphthalocyanine compounds of the formula (1) employed in the process according to the invention have an extremely broad spectrum of activity against microorganisms. Thus it is possible to control, in particular, Gram-positive bacteria, but also Gram-negative bacteria or to protect various substrates against attack by these bacteria by means of the process according to the invention. An action against fungi and yeasts is also observed.

Substances which increase the action can also be added in the process according to the invention, inter alia electrolytes, for example inorganic salts, for instance sodium chloride, potassium chloride, sodium sulfate, potassium sulfate, sodium acetate, ammonium acetate, alkali metal phosphates and alkali metal tripolyphosphates, especially sodium chloride and sodium sulfate. These salts can be added to the agents according to the invention or can be added directly in the application process, so that they are present in the application solution in a concentration of, preferably, 0.1 to 10%.

By virtue of the broad spectrum of action mentioned against microorganisms, the process according to the invention or the agents according to the invention can be employed in a number of fields of use, examples of which are listed below.

The sterilisation of textiles of synthetic or natural origin may be mentioned as an important application. Thus, material to be washed in the household or in industry can be disinfected by means of the process according to the invention. The material to be washed can be treated for this purpose in the manner mentioned above with aqueous solutions of the azaphthalocyanine derivatives according to the invention, while being irradiated with light. The azaphthalocyanine dye can advantageously be present in the treatment liquor in a concentration of 0.01 to 50 mg/l. The sterilisation can also be carried out advantageously together with the washing process. For this purpose, the material to be washed is treated with a wash liquor containing customary detergent substances, one or more azaphthalocyanine derivatives according to the invention and, if desired, inorganic salts and/or further substances having an antimicrobial action. The washing process can be carried out manually, for example in a tub, or can be carried out in a washing machine. The necessary exposure to light can be effected during the washing process by means of suitable light sources, or the moist material being washed can also, subsequently, for example during drying, either be exposed to a suitable artifical source of light or simply exposed to sunlight.

The compounds of the formula (1) can be added directly to the disinfection liquor or bleach or wash liquor. They can also be incorporated into soaps or detergents containing known mixtures of detergent substances, for example soap in the form of flakes and powder, synthetics, soluble salts of sulfonic acid half-esters of higher fatty alcohols, arylsulfonic acids containing higher and/or multiple alkyl substituents, sulfocarboxylic acid esters of medium to higher alcohols, fatty acid acylaminoalkylglycerolsulfonates or acylaminoarylglycerolsulfonates, phosphoric acid esters of fatty alcohols and the like, builders, for example alkali metal polyphosphate and polymetaphosphate, alkali metal pyrophosphates, phosphate substitutes, such as Na aluminium silicates, polyacrylates and the like, and additives, such as alkali metal salts of carboxymethylcellulose and other soil-redeposition inhibitors, and also alkali metal silicates, nitrilotriacetic acid, ethylenediaminetetraacetic acid, foam stabilisers, such as alkanolamides of higher fatty acids, and, if desired, antistatic agents, fat-restoring skin protection agents, such as lanolin, enzymes, perfumes and dyes, fluorescent brighteners, further inorganic salts and/or further antimicrobial active substances or bleaching agents.

The process according to the invention can also be used to impart an antimicrobial finish to textiles, since the azaphthalocyanine derivatives according to the invention are readily absorbed by the fibres and ensure a long-lasting effect.

A further field of use for the process according to the invention and for the agents according to the invention is the disinfection of hospital linen, medical articles for daily use and pieces of equipment and floors, walls and furniture (surface disinfection) both generally and particularly in hospitals. The disinfection of hospital linen can be carried out in the manner described above for general material to be washed. The other articles, and also the surfaces of floors and walls, can be treated with aqueous solutions containing azaphthalocyanine compounds according to the invention, and, in the course thereof or subsequently, can be exposed to suitable sources of light. The disinfection solutions can, in addition, also contain detergent substances, other compounds having an antimicrobial action and/or inorganic salts.

Surface disinfection can be achieved, for example, by applying (for example by spraying) to the appropriate surface, an aqueous solution of the azaphthalocyanine compounds according to the invention, this solution preferably containing about 0.001–50 ppm of active substance. The solution can also contain, in addition, other customary additives, for example wetting agents, dispersing agents or emulsifiers, detergent substances and, if desired, inorganic salts. After the solution has been applied, the surface is simply exposed to sunlight or, if required, it can in addition be irradiated by means of an artificial source of light, for example an incandescent lamp. It is advisable to keep the surface moist during the exposure to light.

The process according to the invention and/or the agents according to the invention can also be employed with advantage for sterilising or disinfecting swimming baths. For this purpose it is advantageous to add one or more of the compounds of the formula (1), preferably in an amount of 0.001 to 50, in particular 0.01 to 10, ppm to the water in the swimming bath. Exposure is effected merely by means of sunlight. If desired, additional exposure by means of builtin lamps can be provided. It is possible, by means of the process described, to keep the water in swimming pools free from undesirable germs and to maintain the quality of the water in an excellent state.

The process according to the invention can also be used for sterilising effluents from sewage treatment plants. This is effected by adding to the effluent, for example, 0.001–100, in particular 0.01–10, ppm of one or more of the compounds of the formula (1). Irradiation is advantageously effected by means of sunlight; if desired, additional irradiation can be carried out by means of artifical sources of light.

The possible uses mentioned above represent only an exemplary enumeration of the very wide applicability of the process according to the invention and thus of the azaphthalocyanines, according to the invention, of the formula (1).

The process according to the invention is particularly preferred for bleaching and removing spots from textiles.

The bleaching and spot-removal process according to the invention, in which the azaphthalocyanine compounds according to the invention are used, i.e. the treatment of textiles with these compounds, is preferably carried out in an aqueous liquor and especially in a neutral or alkaline pH range.

The azaphthalocyanines according to the invention are advantageously employed in amounts of 0.01 to 100, in particular 0.01 to 50, mg/l of treatment liquor, it being possible for the amount employed to vary depending on the number of groups imparting solubility in water and on the nature of the substituent Y.

The process is preferably carried out as a combined washing and bleaching process, in which case the aqueous liquor also contains an organic washing agent, such as soap or synthetic washing agents (detergent substances) and, if desired, also other washing agent additives, such as soil-suspending agents, for example sodium carboxymethylcellulose, complex-formers, such as sodium tripolyphosphate, sodium silicate and sodium ethylenediaminetetraacetate and fluorescent brightening agents. Examples of suitable detergent substances are those which have been enumerated earlier in the text in connection with the use of the compounds of the formula (1) in disinfection liquors or bleach or wash liquors and in connection with the relevant washing agents. The azaphthalocyanine according to the invention can, therefore, either be already incorporated in the appropriate washing agent or can be added subsequently to the wash liquor. The process can, however, also be carried out as a bleaching process alone, without the addition of washing agents. In this case it is advantageous for the treatment liquor to contain an electrolyte, for example sodium chloride, sodium sulfate or sodium tripolyphosphate, in order to ensure the absorption of the azaphthalocyanine dye. The amounts of electrolyte can be about 0.5 to 20 g/l.

As mentioned above, the wash or bleach liquors can, if desired, also contain one or more fluorescent brighteners. These can be customary fluorescent brighteners for washing agents. It is preferable, however, to employ fluorescent brighteners belonging to the classes comprising distyrylbiphenylsulfonic acids and salts thereof and/or 4,4'-bis-(1,2,3-triazol-2-yl)-stilbenedisulfonic acids and salts thereof. Very particularly good bleaching effects which are higher than would be expected from the additive action of the individual components are achieved by means of these fluorescent brighteners in combination with the photoactivators according to the invention. Suitable fluorescent brighteners of this type are, in particular, those of the formula (A1) indicated later in the text, for example those of the formula (A2) and very particularly preferentially those of the formula (A3). Fluorescent brighteners of the formula (A4) also produce good results, as do mixtures of the fluorescent brighteners of the formulae (A3) and (A4).

The bleaching process according to the invention is advantageously carried out at temperatures within the range from about 20 to 100, in particular 20° to 85° C., for a period of time amounting to 15 minutes to 5 hours, preferably 15 minutes to 60 minutes.

The presence of oxygen and irradiation with light is necessary for the bleaching process according to the invention. The oxygen dissolved in the water or present in the atmosphere is sufficient as a source of oxygen.

Irradiation can be effected by means of an artificial source of light (for example an incandescent lamp or infrared lamp), and it is possible to irradiate the bleach or wash liquor directly, either by means of a light source within the container in which the liquor is present (for example a lamp in the washing machine), or by means of a light source outside the container. Equally, however, it is also possible to carry out the irradiation only after the textiles have been removed from the treatment liquor. In this case, however, the textiles should still be moist or they must be re-moistened subsequently. Sunlight can, however, be used with particular advantage as the source of light, the textiles being exposed to sunlight either during a treatment in the steeping liquor or, in a moist state, after the treatment in the wash or bleach liquor. The source of light used should preferably supply light within a wavelength range of 300–800 nm.

Although the compounds of the formula (1) generally produce very good bleaching effects, those which are substituted by groups of the formulae $SO_3^{\ominus}$, $COO^{\ominus}$, $SO_2^{\ominus}$, $SO_2^{\ominus}NCN$ and $SO_2^{\ominus}N-SO_2-R_6$ and especially those in which $E=SO_3^{\ominus}$, are preferred for use in customary washing, bleaching and steeping agents which usually contain anionic and/or nonionic detergent substances.

The process, according to the invention, for bleaching by means of compounds of the formula (1) can also be carried out in the presence of reducing agents. This "reductive" bleaching can in some cases (depending on the substrate, type of dirt and the like) produce an improvement in the bleaching effect. It is preferable to use a reducing agent which has a reduction potential $E_o$ <3.0 eV, in particular <0.8 eV. These reducing agents can be added directly to the bleach (wash) liquor or they can be already present in appropriate washing, steeping, rinsing or bleaching agents together with the photobleaching agent and the customary detergent substances and other washing agent ingredients. The addition of the reducing agents mentioned is particularly advantageous if the photobleaching is carried out in the steeping process. Preferred reducing agents which are suitable in the bleaching process according to the invention are described below in the description of the agents containing the photoactivators according to the invention. The present invention also relates to photosensitising (photoactivating) agents and/or agents producing singlet oxygen which contain one or more of the azaphthalocyanine compounds defined in formula (1).

The present invention also relates, therefore, to agents for carrying out the process according to the invention, in particular agents having an antimicrobial action, and to bleaching, washing, rinsing and steeping agents. These agents contain one or more azaphthalocyanine compounds, according to the invention, of the formula (1). In addition, depending on the mode of use, the said agents can also contain customary formulation ingredients.

Preferred agents of this type contain one or more azaphthalocyanine compounds according to the invention, one or more inorganic salts, for example NaCl, KCl, NaBr, KBr, $K_2SO_4$, $Na_2SO_4$, $K_2CO_3$, $Na_2CO_3$, $NaHCO_3$ and others, in particular NaCl and/or $Na_2SO_4$, and, if desired, water. For example, an agent of this type consists of about 1–80% of a compound of the formula (1), 1–40% of NaCl and/or $Na_2SO_4$ and 0–95% of water. These agents can thus be in a solid form (for example granules) or as an aqueous solution, for example in the form of a 5–50%, for example 5–20%, solution.

In addition to the azaphthalocyanine active substance, washing, steeping and rinsing agents according to the invention and having a bleaching action contain, for example, customary ingredients of washing agents, for example one or more organic detergents, if desired alkaline builder salts and, if desired, further bleaching agents, for example per compounds, for instance a perborate, percarbonate and the like.

The washing agents or steeping agents according to the invention contain, for example, the known mixtures of detergent substances, for example soap in the form of flakes and powders, synthetics, soluble salts of sulfonic acid half-esters of higher fatty alcohols, arylsulfonic acids containing higher and/or multiple alkyl substituents, sulfocarboxylic acid esters of medium to higher alcohols, fatty acid acylaminoalkylglycerolsulfonates or acylaminoarylglycerolsulfonates, phosphoric acid esters of fatty alcohols and the like. Examples of suitable additives, complex-formers, bleaching agents and the like are alkali metal salts of carboxymethylcellulose and other soil-redeposition inhibitors, and also alkali metal silicates, alkali metal carbonates, alkali metal borates, alkali metal perborates, alkali metal percarbonates, nitrilotriacetic acid, ethylenediaminotetraacetic acid and foam stabilisers, such as alkanolamides of higher fatty acids. The following, for example, can also be present in the washing agents: antistatic agents, fat-restoring skin protection agents, such as lanolin, enzymes, antimicrobial agents, perfumes and fluorescent brighteners.

As already mentioned, the washing agents or bleaching agents according to the invention can also contain fluorescent brighteners. Suitable brighteners of this type are any of the fluorescent brighteners customary in the washing agent industry. On the other hand, fluorescent brighteners belonging to the classes comprising distyrylbiphenylsulfonic acids and their salts and/or 4,4'-bis-(1,2,3-triazol-2-yl)-2,2'-stilbenedisulfonic acids and salts and mixtures thereof are employed particularly preferentially in washing or bleaching agents according to the invention. If agents according to the invention contain such fluorescent brighteners, the latter are preferably present in the agents in an amount of 0.005–1.5% in particular 0.01–0.5%, based on the total weight of the agent. Fluorescent brighteners which can be employed are, in particular, those of the formula

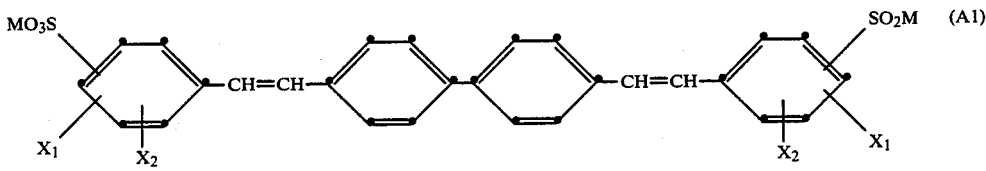

The washing agents or steeping agents according to the invention preferably contain the azaphthalocyanine compounds of the formula (1) in an amount of 0.0005 to 1.5, in particular 0.005–1%, by weight, based on the total washing or steeping agent.

in which $X_1$ is hydrogen, chlorine, bromine or alkyl or alkoxy, each of which has 1 to 4 C atoms, $X_2$ is hydrogen or alkyl having 1 to 4 C atoms and M is hydrogen or an alkali metal ion, ammonium ion or amine salt ion, especially those of the formula

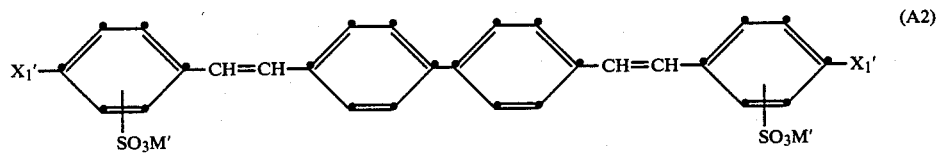

Washing or steeping agents according to the invention and having a bleaching action contain, for example, 0.005–1% by weight of the said azaphthalocyanine compounds, 10–50% by weight of an anionic, nonionic, semipolar, ampholytic and/or zwitter-ionic surface-active substance, 0–80% of an alkaline builder salt and, if desired, further customary ingredients of washing agents, for example those mentioned above.

Examples of surface-active substances in the said agents are also water-soluble alkylbenzenesulfonates, alkyl-sulfates, ethoxylated alkyl ether-sulfates, paraffinsulfonates, α-olefinsulfonates, α-sulfocarboxylic acids, salts and esters thereof, alkyl glyceryl ether-sulfonates, fatty acid monoglyceridesulfates or monoglyceridesulfonates, alkylphenol polyethoxy-ether-sulfates, 2-acyloxyalkanesulfonates, β-alkyloxyalkanesulfonates, soaps, ethoxylated fatty alcohols, alkylphenols, polypropoxyglycols, polypropoxyethylenediamines, amine oxides, phosphine oxides, sulfoxides, aliphatic secondary and tertiary amines, aliphatic quaternary ammonium, phosphonium and sulfonium compounds or mixtures of the said substances.

Examples of alkaline builder salts, which can be present in the agents according to the invention, for instance, in an amount of 10–60% by weight are, inter alia: water-soluble alkali metal carbonates, borates, phosphates, polyphosphates, bicarbonates and silicates, water-soluble aminopolycarboxylates, phytates, polyphosphonates and polycarboxylates and water-insoluble aluminium silicates.

in which $X'_1$ is hydrogen or chlorine and $M'$ is hydrogen, sodium, potassium or ammonium, and preferably of the formula

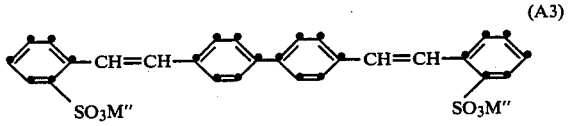

in which $M''$ is hydrogen, sodium or potassium, and/or of the formula

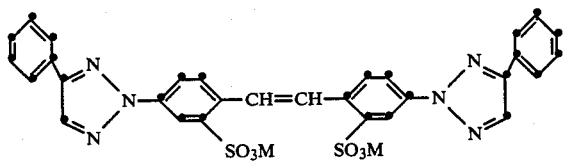

in which M is hydrogen or an alkali metal ion, ammonium ion or amine salt ion.

The washing agents, according to the invention, having an antimicrobial activity generally contain the azaphthalocyanine compounds according to the invention in an amount of 0.0005 to 1.5, in particular 0.005 to 1%, by weight, based on the total washing agent.

In other respects washing agents, according to the invention, having an antimicrobial action can have the same composition as described earlier in the text for the washing and steeping agents, according to the invention, having a bleaching action.

In the washing/bleaching and steeping agents described above which contain, as detergent substances, especially anionic, nonionic, semipolar, ampholytic and/or zwitter-ionic surface-active substances, it is preferable to use azaphthalocyanine compounds of the formula (1) which contain anionic groups of the formula $SO_3^\ominus$, $COO^\ominus$, $SO_2^\ominus$, $SO_2^\ominus NCN$ or/and $SO_2^\ominus N-SO_2-R_6$, in particular $SO_3^\ominus$.

All the washing, rinsing, steeping and after-treatment agents according to the invention, having a bleaching action and described above, which contain one or more azaphthalocyanines of the formula (1) as photobleaching agents, can, if desired, additionally contain a reducing agent. Depending on the dirt and substrate to be treated, the presence of such an agent improves the bleaching action of the photoactivator in some cases. Application is effected in a customary manner (irradiation with light). Particularly good results are achieved using this "reductive bleaching" in the steeping process. For this purpose, the textiles are steeped in a liquor containing the steeping (washing) agent together with the photoactivator and the reducing agent, and are irradiated directly with light, preferably with sunlight.

Suitable reducing agents are substances such as are defined and described as electron donors in EP-A No. 87,833. In particular, reducing agents having a reduction potential of <3.0 eV, especially <0.8 eV, can be used. Examples of reducing agents of this type (electron donors) are alkali metal sulfites, cysteine, alkali metal thiosulfates, Fe(II) salts, such as FeSO4, Sn(II) salts, such as SnCl2, and the like. Of these alkali metal sulfites, in particular sodium sulfite, are preferred. If a reducing agent (electron donor) mentioned above is present in washing, bleaching, steeping or rinsing agents according to the invention, its concentration is, for example, 1 to 40% by weight, based on the total agent.

If, according to the process principle (B) described above, the compounds according to the invention, of the formula (1), are prepared by introducing the groups EZ, imparting solubility in water, into the corresponding azaphthalocyanine pigments insoluble in water, these pigments are required as starting materials. These are of the formula (3) indicated above. Some of these pigments are known, namely some zinc tetraazaporphyrazines; see, for example, C.A. 76 (1972), 140752r, C.A. 72 (1970), 112779d, C.A. 91 (1979), 203526c, C.A. 94 (1981), 83264d and C.A. 98 (1983), 41394y. However, the majority of them are novel.

The novel azaphthalocyanine pigments of the formula (3) are also the subject of the present invention. They are of the general formula

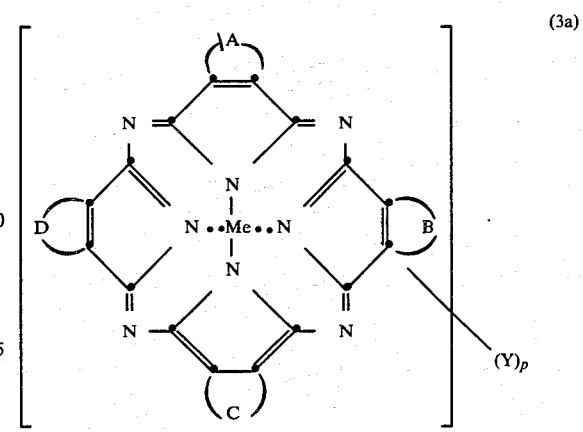

in which Me is Al(III), Zn(II), Ge(IV) or Sn(IV), A, B, C or D independently of one another complete a benzene ring or a ring of the formula

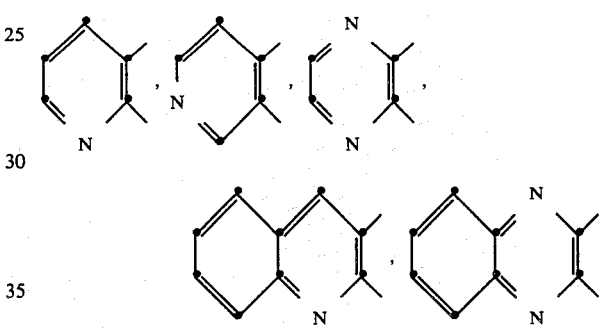

at least one of the rings completed by A, B, C and D being one of the said heterocyclic rings, Y is a halogen and p is any desired number from 0 to 2, with the proviso that Me is other than Zn(II) if A, B, C and D are identical and complete one of the said heterocyclic rings and simultaneously p is 0.

With respect to the rings completed by A, B, C and D, the same partial structures are possible as those described at the outset under formula (1). The 2,3-pyridine ring is preferred as the heterocyclic ring.

The number of heterocyclic rings is preferably 1 or 2, and the remaining rings (3 or 2) are then benzene rings.

Examples of fused heterocyclic rings A, B, C and/or D (including benzo or naphtho rings which may be fused to them) are those of the formulae

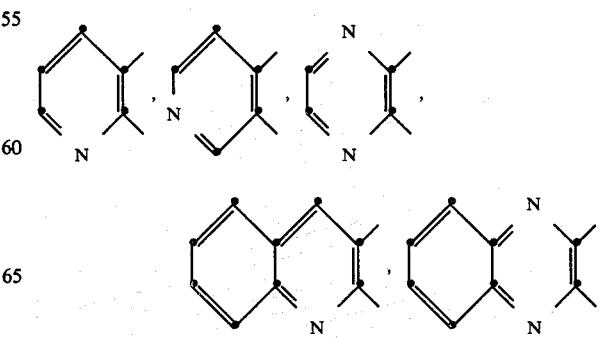

Those compounds of the formula (3a) are particularly preferred in which one or two of the rings completed by A, B, C and D are of the formula

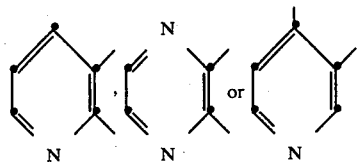

and the remaining (3 or 2) rings are benzene rings.

The explanations given in connection with formula (1) apply to the central atoms (central atom groupings).

The preferred central atoms are Zn(II), Al(III), Sn(IV) and Ge(IV), in particular Al(III) or Zn(II).

In the azaphthalocyanines of the formula (3a), according to the invention, Y has the same preferred meanings as in formula (1). In particular, p is any desired number from 0 to 2, but preferably 0.

The azaphthalocyanines of the formula (3a) can be obtained by processes known per se. The synthesis of the appropriate azaphthalocyanine ring skeleton can be carried out analogously to that of the non-heterocyclic phthalocyanine ring skeleton, for example as described in Ullmann's Encyclopädie der technischen Chemie [Ullmann's Encyclopaedia of Industrial Chemistry], 4th Edition, Volume 18, pages 501 et seq., and by F. H. Moser, A. L. Thomas, "Phthalocyanine" (1963), pages 104 et seq. For the incorporation of nitrogenheterocyclic structures, the appropriate ortho-dicarboxylic acids (or derivatives thereof) of the desired nitrogenheterocyclic structures are required in place of the corresponding phthalic acid derivatives. If A, B, C and D are identical, 4 molar equivalents of the corresponding dicarboxylic acid derivatives are used. In the case of "mixed" azaphthalocyanines (for example different heterocyclic structures A, B, C, D or mixtures of benzo rings and hetero rings A, B, C and D), the appropriate dicarboxylic acid derivatives are employed in the desired molar mixing ratio.

Methods for the preparation of azaphthalocyanines are also to be found in the C.A. references given above before formula (3a), and in DE-A No. 879,100, DE-A No. 2,441,648 and J. Am. Chem. Soc. 85 (1963), 668–671.

The process for the preparation of azaphthalocyanines, according to the invention, of the formula (3a) comprises condensing ortho-dicarboxylic acids of the formulae

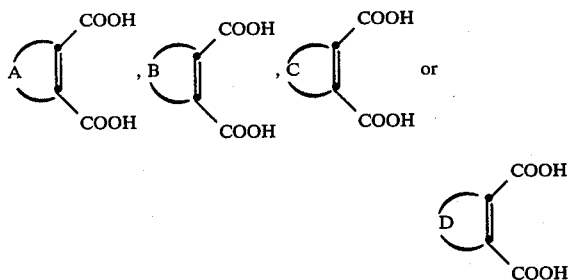

or derivatives thereof, which may carry substituents Y, by the methods customary in phthalocyanine chemistry to give the corresponding azaphthalocyanine ring system, it being possible for the abovementioned carboxylic acids or derivatives thereof to be identical or different and, in the latter case, the quantitative molar ratio being chosen such that the desired ratio of A, B, C and D is reached in the resulting azaphthalocyanine, it being possible for the dicarboxylic acids to contain substituents Y, if desired, and the process being carried out in the presence of a compound, for example a salt, of the element Me or the central atom Me being introduced subsequently into the azaphthalocyanine without a central atom.

Examples of derivatives of the said ortho-dicarboxylic acids are: dinitriles, anhydrides, imides and derivatives of the type of 1-amino-3-imino-isoindolenines. The free carboxylic acids or their salts can also be used as starting materials.

If ortho-dinitriles are used as the starting materials, these are cyclised, advantageously in the presence of a salt of the element Me, in the melt or in solution or suspension to give the desired azaphthalocyanine. If no salt of the element Me is added, the central atom must be introduced subsequently (see method A described above).

If the ortho-dicarboxylic acids or their salts, their anhydrides or imides are used as the starting materials, the cyclisation is carried out in the presence of urea (urea method). The reaction is advantageously carried out in the melt, but it can also take place in a solvent. Advantageously, the reaction is carried out at an elevated temperature, for example at a temperature of 50°–250° C., preferably between 100° and 200° C. (These preferred temperature ranges also apply to the cyclisation of the dinitriles, described above). Preferably, the reaction is carried out in the presence of a salt of the element Me, whereupon the azaphthalocyanine with the central atom is formed directly. It is particularly advantageous also to add a catalyst, for example boric acid or in particular ammonium molybdate, in addition to urea.

The o-dicarboxylic acid derivatives of the type of 1-amino-3-iminoisoindolenines, which can also be used as starting compounds, are of the formulae

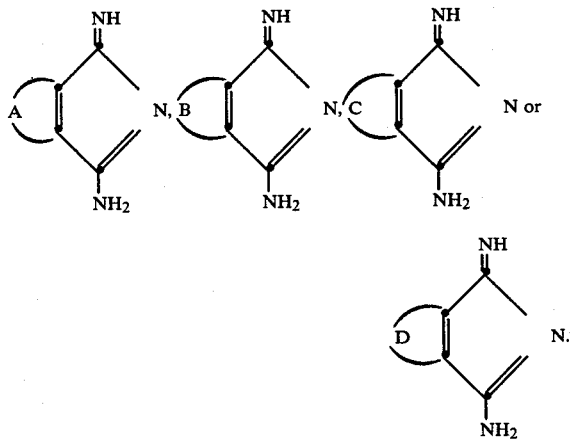

The cyclisation of these derivatives to give the azaphthalocyanine ring system is likewise carried out advantageously in the presence of a salt of the element Me and preferably at an elevated temperature, for example between 50° and 250°C., in particular between 100° and 200° C. This cyclisation can also be carried out in the melt, but reaction in an organic solvent is preferred.

Further preferred reaction parameters both for this process and the two above-mentioned processes (dinitrile and urea methods) are shown, inter alia, in DE-A No. 879,100 and in the preparation examples which follow below.

The substituent Y in the compounds of the formula (3a) (unless p is 0 anyway) can already be present in the starting materials and can therefore be introduced directly into the azaphthalocyanine ring system during its synthesis. It can also be introduced subsequently by substitution reactions, and this is possible especially in the case of halogen atoms by subsequent halogenation. Certain substituents, namely chlorine, can also be introduced into the ring system during the cyclisation reaction, if this is carried out, for example, in the presence of chlorides of the element Me. This effect can be observed in particular when o-dinitriles are used as the starting material, for example if the reaction is carried out in the presence of AlCl$_3$.

The abovementioned ortho-dicarboxylic acids and their derivatives, required as starting compounds, are known or can be obtained by processes known per se. Some of these are described, for example, in DE-A No. 879,100, in particular those of the type of 1-amino-3-imino-isoindolenines.

The azaphthalocyanine pigments, according to the invention, of the formula (3a) can be used as intermediates for the preparation of the water-soluble azaphthalocyanines of the formula (1). However, they themselves also show excellent photosensitising (photoactivating) properties and are outstanding singlet oxygen producers. Since they are insoluble in water, however, they can develop these effects only in those systems in which they are sufficiently soluble, i.e. for example in certain organic solvents or in heterogeneous systems if they are actively dispersed, for example, on or in a carrier. Such a heterogeneous sensitiser can also be active in aqueous systems. Heterogeneous sensitisers of this type can be prepared by means of the azaphthalocyanine pigments, according to the invention, of the formula (3a) and by using them in the manner described in DE-A No. 3,006,886.

The present invention thus also relates to the use of the azaphthalocyanines of the formula (3a) as photosensitisers, photoactivators or singlet oxygen producers in organic systems, in which they are soluble, or in heterogeneous systems, and to a process for carrying out a photosensitised (photoactivated) reaction or a reaction with singlet oxygen, wherein one or more azaphthalocyanines of the formula (3a) are, in the presence of oxygen, brought into contact with the medium in or on which the said reaction is intended to take place and which dissolves the azaphthalocyanines or in which the latter are present in an actively dispersed form, or are incorporated into this medium and irradiated with light.

The examples below illustrate in greater detail the processes for the preparation of the azaphthalocyanine compounds according to the invention, the use of the latter and agents containing them, without thereby expressing a limitation to the subject matter of these examples. In the examples, just as in the remainder of the description, parts and percentages are always by weight, unless stated otherwise. The $\lambda_{max}$ values given in the preparation examples were determined in dimethylformamide, unless stated otherwise.

EXAMPLE 1

0.05 mol of 4- or 7-aza-1-amino-3-iminoisoindolenine nitrate (known from DE-A No. 879,100, Example 14), 0.15 mol of 1-amino-3-iminoisoindolenine nitrate (known from DE-A No. 879,100, Example 3) and 0.05 mol of aluminium acetate are introduced into a mixture of 100 ml of 1,2-dichlorobenzene and 100 ml of N,N-dimethylaniline. The reaction mixture is heated up to 175° C. within 3 hours and then stirred at this temperature for 1½ hours. The product which has precipitated is filtered off at room temperature with suction and washed with 200 ml of acetone. The residue is then stirred for ½ hour at 75° C. in 10% sodium hydroxide solution, filtered off with suction and washed with water until neutral. This gives 19 g of the azaphthalocyanine of the formula

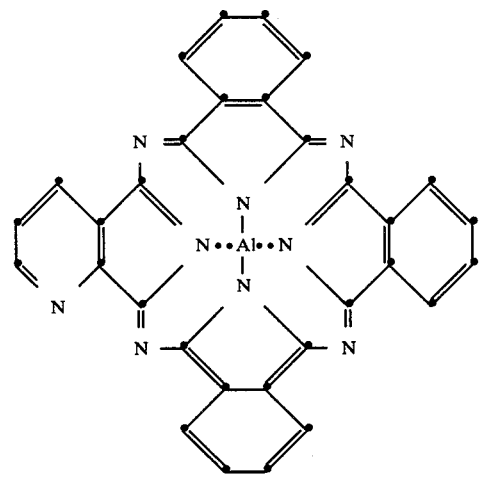

(101)

EXAMPLE 2

The procedure of Example 1 is repeated, except that 0.1 mol of 4- or 7-aza-1-amino-3-iminoisoindolenine nitrate and 0.1 mol of 1-amino-3-iminoisoindolenine nitrate are employed, affording an aluminium azaphthalocyanine of the formula

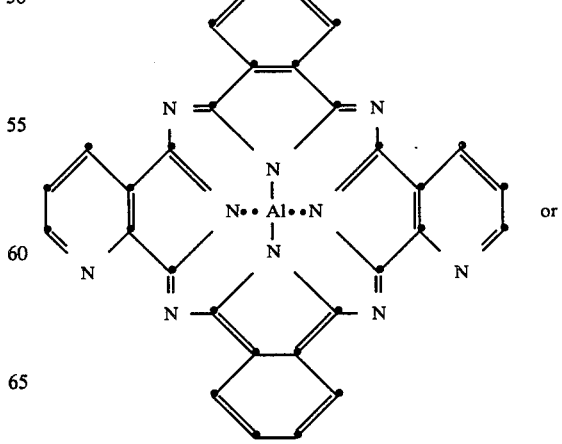

(201)

or

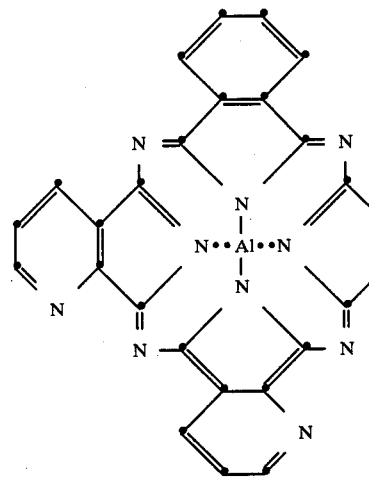

EXAMPLE 3

The procedure of Example 1 is repeated, using 0.05 mol of ZnCl$_2$ instead of aluminium acetate, affording the azaphthalocyanine of the formula (101) in which Al is replaced by Zn (=compound No. 301).

EXAMPLE 3a

The procedure of Example 2 is repeated, using 0.05 mol of ZnCl$_2$ instead of aluminium acetate, affording the azaphthalocyanine of the formula (201) in which Al is replaced by Zn (=compound No. 302).

EXAMPLE 4

20 g of the azaphthalocyanine of the formula (101), obtained in Example 1, are introduced into 200 ml of chlorosulfonic acid. The reaction temperature is increased to 130° to 135° C. within 2 hours, with stirring, and then held for 5 hours. After cooling to 70° C., 41 ml of thionyl chloride are added dropwise and the reaction mixture is stirred under reflux at 85° to 90° C. The cooled reaction mixture is discharged onto ice/water. The product which has precipitated is filtered off with suction and washed with ice water. The residue is stirred up in 500 ml of water, and the suspension is adjusted with sodium hydroxide solution to pH 10 and heated at 80° C. until the residue has completely dissolved. The solution obtained is evaporated to dryness in vacuo. This gives the sulfonated aluminium azaphthalocyanine of the approximate formula

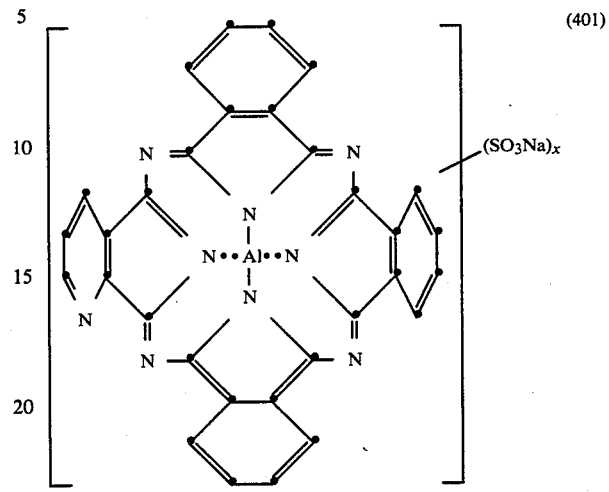

in the form of a powder readily soluble in water.

$\lambda_{max}$=672nm; x is a number of about 1.5 to 3.5.

EXAMPLE 4a 20 g of the azaphthalocyanine of the formula (201), obtained in Example 2, are sulfonated as described in Example 4. This gives the sulfonated aluminum azaphthalocycanine of the approximate formula

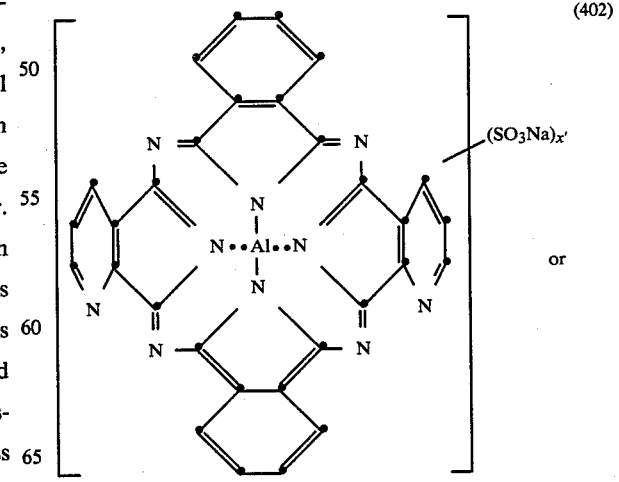

or

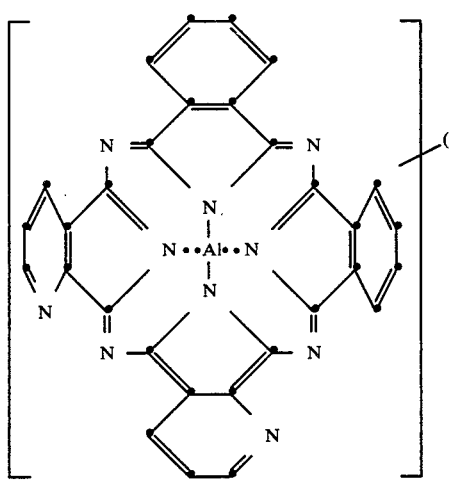

in which x' is a number of about 1 to 2.5. $\lambda_{max}$=659 nm.

EXAMPLE 4b 20 g of the azaphthalocyanine (compound No. 301) obtained in Example 3 are sulfonated as described in Example 4. This gives the azaphthalocyanine of the formula (401), in which Al is replaced by Zn (=compound No. 403), with $\lambda_{max}$=666 nm.

EXAMPLE 4c 20 g of the azaphthalocyanine (compound No. 302) obtained in Example 3a are sulfonated as described in Example 4. This gives the azaphthalocyanine of the formula (402), in which Al is replaced by Zn (=compound No. 404), with $\lambda_{max}$=655 nm.

EXAMPLE 5

0.3 mol of phthalic anhydride, 0.1 mol of pyridine-3,4-dicarboxylic acid and 1.5 g of ammonium molybdate are introduced into a melt of 70 g of urea. The mixture is stirred for 15 minutes at 160° C. and then treated with 70 g of urea and 0.1 mol of AlCl₃. The melt solidifies after stirring for about two hours. The mixture is then kept at 180° to 190° C. for 12 hours, without stirring. After cooling, the mass is treated at 20° C. with 800 ml of water, heated at 80° C. for 1 hour and then filtered. The residue is once more stirred up in 1,000 ml of water at 80° C. and filtered off. For further purification, the product is taken up three times in 1,000 ml of water adjusted with sodium hydroxide solution to pH 11 and filtered off. Finally, the filter residue is washed with water until neutral and dried. This gives an azaphthalocyanine of the formula

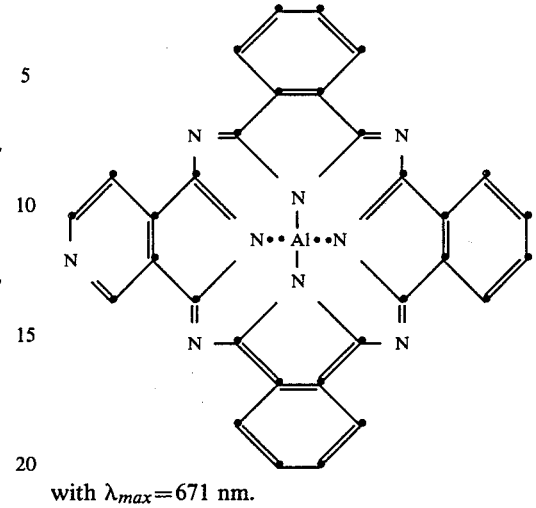

with $\lambda_{max}$=671 nm.

EXAMPLE 5a

The procedure of Example 5 is repeated, except that 0.2 mol of pyridine-3,4-dicarboxylic acid and 0.2 mol of phtahlic anhydride are employed, affording an aluminium azaphthalocyanine of the formula

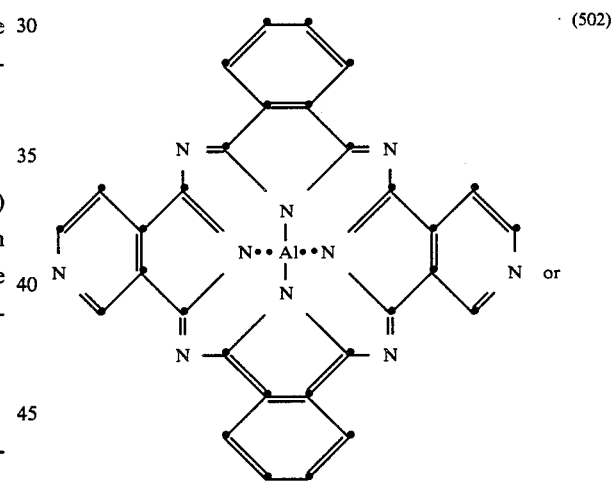

or

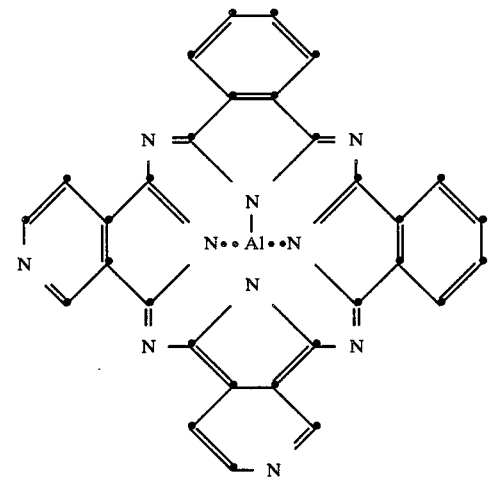

with $\lambda_{max} = 674$ nm.

Example 5b

The procedure of Example 5 is repeated, except that 0.1 mol of GeCl₄ is employed instead of AlCl₃, affording the azaphthalocyanine of the formula (501), in which Al is replaced by Ge (=compound No. 503), with $\lambda_{max} = 674$ nm.

EXAMPLE 5c

The procedure of Example 5 is repeated, except that 0.1 mol of ZnCl₂ is employed instead of AlCl₃, affording the azaphthalocyanine of the formula (501), in which Al is replaced by Zn (=compound No. 504), with $\lambda_{max} = 673$ nm.

EXAMPLE 6

20 g of each of the compounds No. (501), (502), (503) and (504) according to Examples 5, 5a, 5b and 5c are sulfonated by the process described in Example 4. In this way, the sulfonated azaphthalocyanines of the following formulae are obtained:

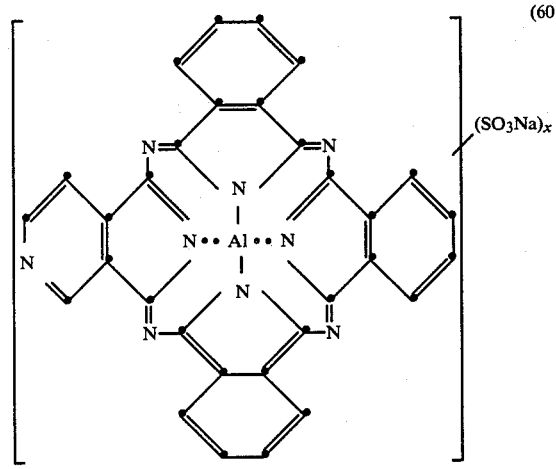

or

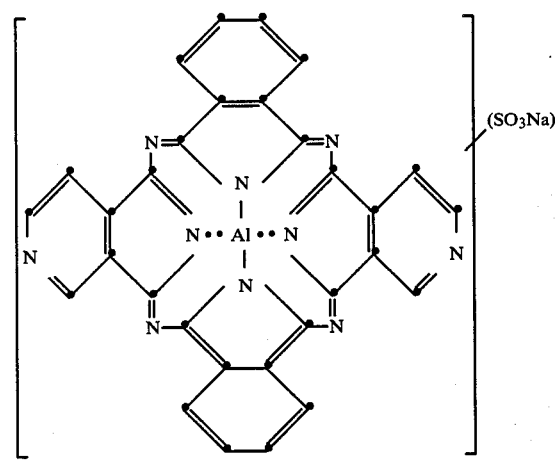

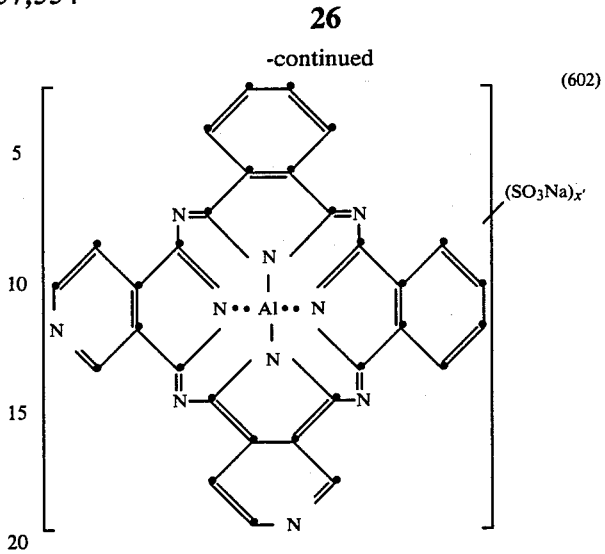

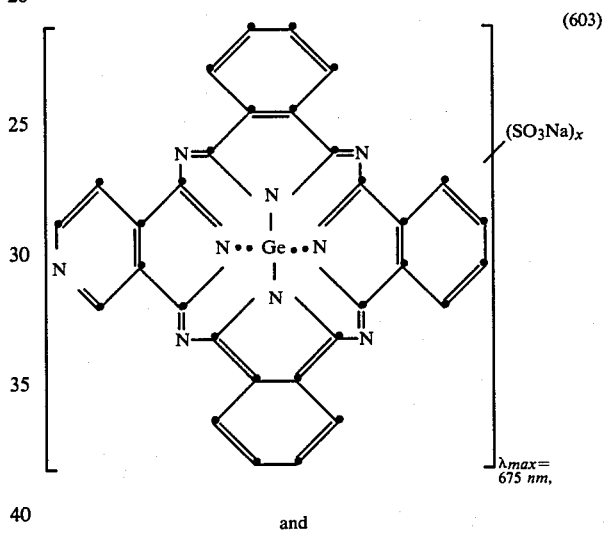

and

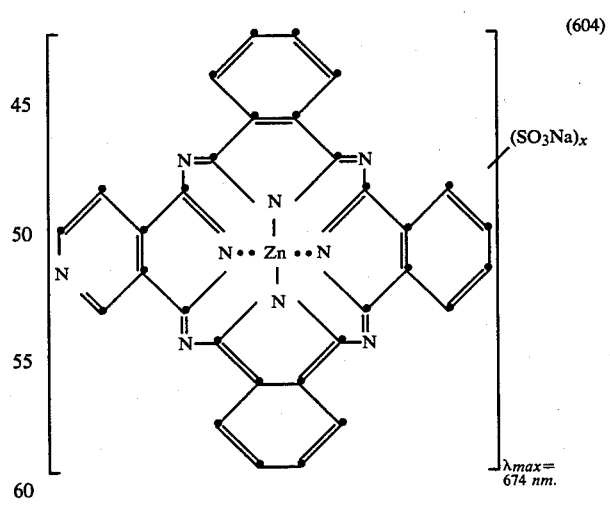

In the above formulae, x is a number of about 1.5 to 3.5, and x' is a number of about 1 to 2.5.

EXAMPLE 7

0.2 mol of 4- or 7-aza-1-amino-3-iminoisoindolenine and 10 g of aluminium acetate are introduced into a mixture of 120 ml of 1,2-dichlorobenzene and 120 ml of N,N-dimethylaniline. The reaction mixture is heated to 175° C. and stirred at this temperature for 1 hour. The reaction mixture obtained is filtered and the residue is washed with acetone. After drying, this gives aluminium tetra-2,3-pyridino-tetraazaporphine of the formula

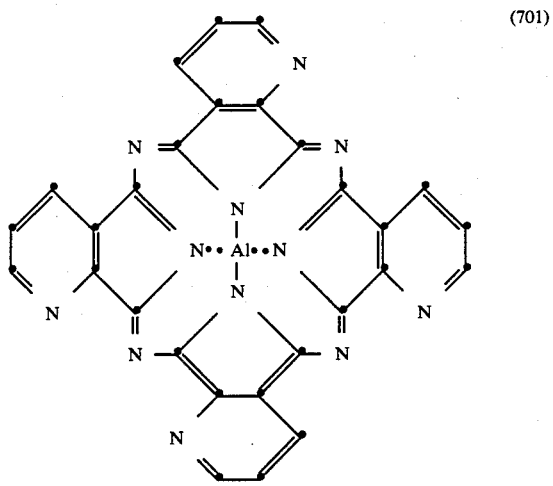

(701)

as a blue powder with $\lambda_{max}=645$ nm.

EXAMPLE 8

60 g of urea are melted at 160° C. in a stirred flask; 69 g of pyridine-3,4-dicarboxylic acid and 1 g of ammonium molybdate are then introduced. After brief stirring, 14 g of AlCl₃ are added slowly, followed by a further 30 g of urea. The reaction mixture is stirred at 170° to 180° C. for 10 hours. For purification, the cooled-down and solidified reaction mixture is comminuted and stirred up for 1 hour at 60° C. in a solution of 1,000 ml of water and 15 ml of concentrated sodium hydroxide solution. The suspension is filtered with suction, the residue is washed with water and taken up in 500 ml of water, and the mixture is adjusted to pH 5 with hydrochloric acid and stirred at 60° C. for 1 hour. The product is filtered off, and the residue is washed with water and dried. This gives aluminium tetra-3,4-pyridino-tetraazaporphine of the formula

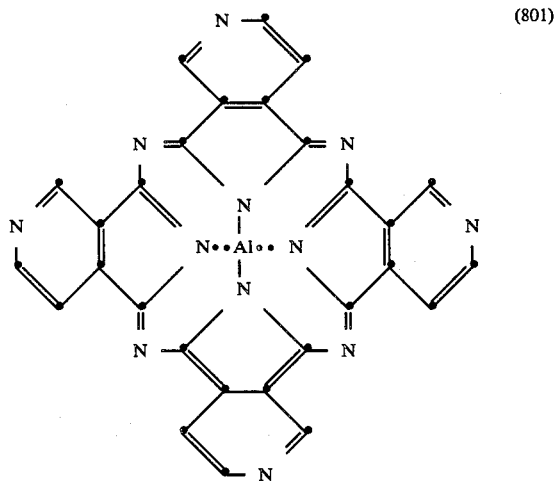

(801)

in the form of a blue powder with $\lambda_{max}=659$ nm.

EXAMPLE 9

0.4 mol of pyrazine-2,3-dinitrile, 0.1 mol of $ZnCl_2$ and 0.5 g of ammonium molybdate are stirred up in 150 ml of ethylene glycol monomethyl ether in a stirred flask. 30 ml of 1,8-diazabicyclo[5.4.0]undec-7-ene (DBU) are then added dropwise, the temperature rising to 65° C. The reaction mixture is stirred at 70° to 75° C. for 6 hours. The product which has precipitated is filtered off and washed with 500 ml of methanol. The filter residue is introduced into a solution of 1,000 ml of water and 40 ml of concentrated hydrochloric acid, heated to 70° with stirring and then filtered off. This operation is repeated twice. The residue is then stirred up six times in a solution of 1,000 ml of water and 40 ml of concentrated sodium hydroxide solution at 70° to 80° C., filtered off, finally washed with 1,000 ml of water and dried. The product is of the formula

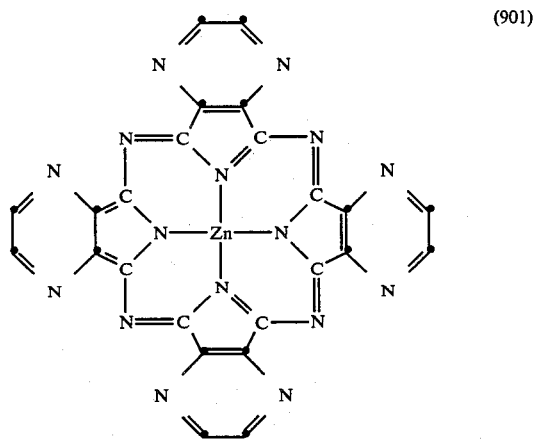

(901)

$\lambda_{max}=635$ nm.

EXAMPLE 10

The procedure described in Example 9 is repeated, using AlCl₃ instead of ZnCl₂. The compound of the formula

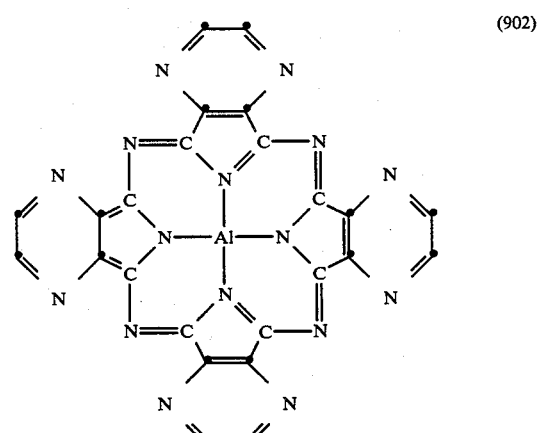

(902)

with $\lambda_{max}=624$ nm (borax buffer) is obtained.

If the procedure described in Example 9 is repeated, partially replacing the pyrazine-2,3-dinitrile by corresponding molar quantities of phthalo-1,2-dinitrile and- /or replacing ZnCl₂ by AlCl₃ and GeCl₄, compounds of the following structures, and their isomers, are obtained:
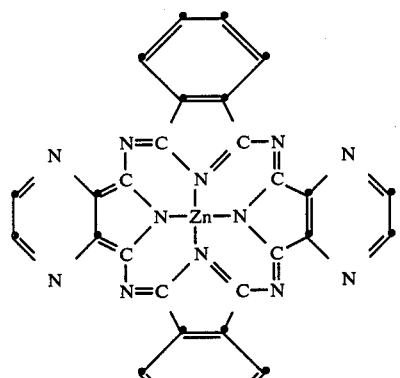
(903)
max λ = 668 nm
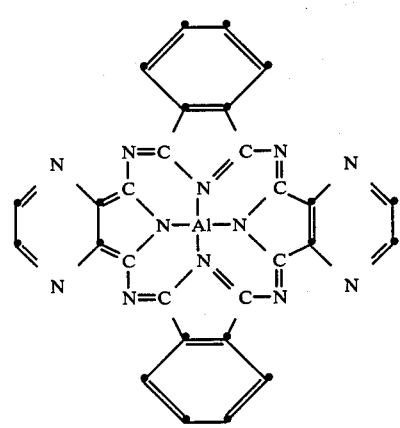
(904)
λ max = 671 nm
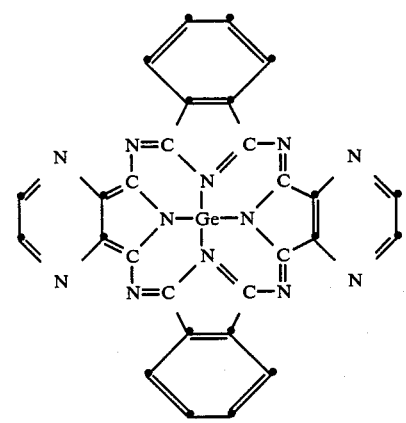
(905)
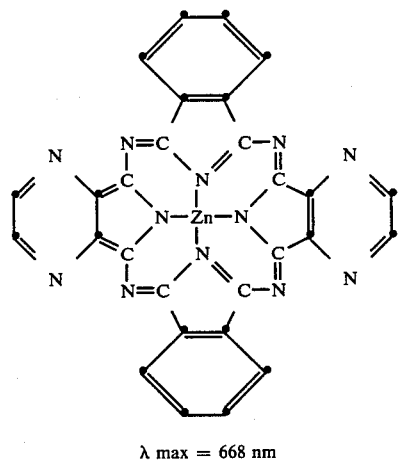
(906)
λ max = 668 nm
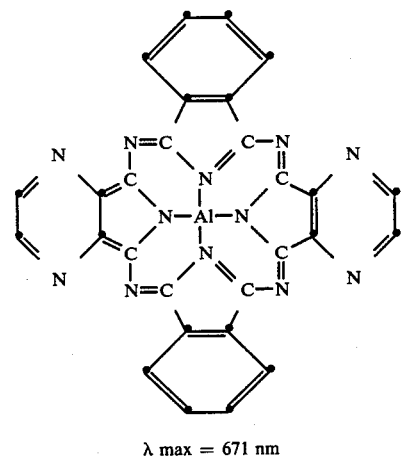
(907)
λ max = 671 nm
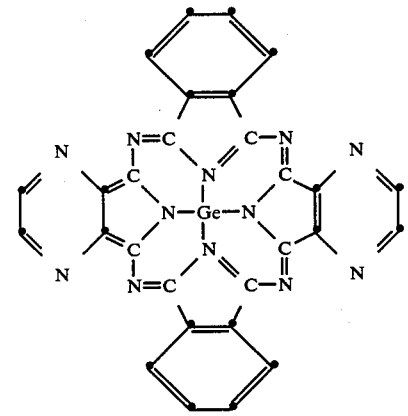
(908)
Sulfonation of the compounds of the formula (903) to (908) by the process described in Example 4 gives the water-soluble compounds, and their isomers, of the formulae:

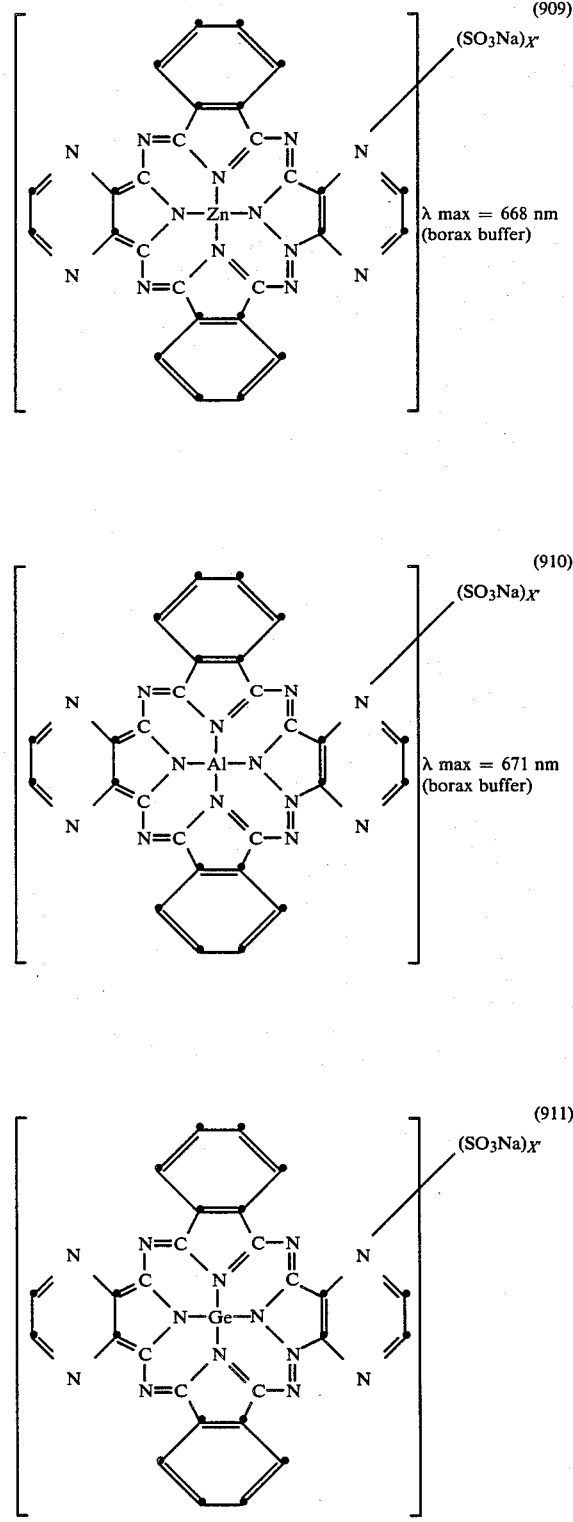
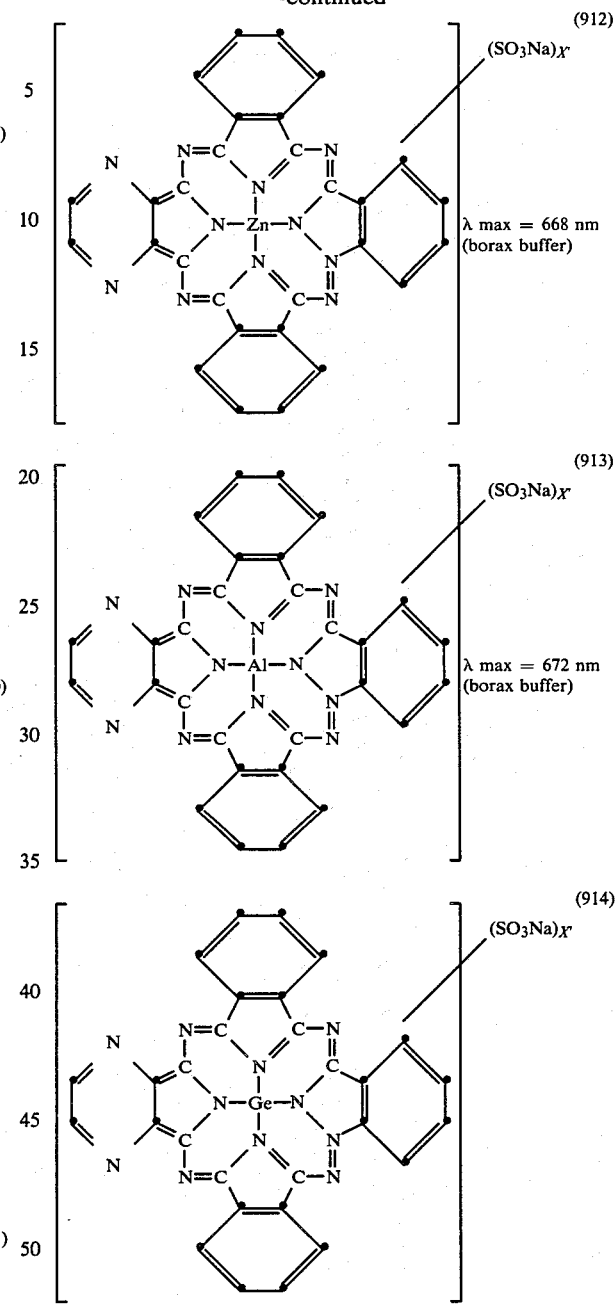

X being a number of 1 to 2.5.

EXAMPLE 11

60 parts of compound (504) are introduced into 260 parts by volume of chlorosulfonic acid, with thorough stirring. The temperature is kept at 20° to 25° C. by external cooling. The reaction mixture is first stirred for half an hour at room temperature; the temperature is then raised within one hour to 110° to 115° C. After half an hour, the reaction temperature is raised to 130° to 135° C. within one hour and maintained for 4 hours. The reaction mixture is then cooled to 70° to 75° C. and treated within 45 minutes with 125 parts by volume of thionyl chloride. Stirring is continued for one further hour at 85° to 90° C., and the reaction mass is then allowed to cool to room temperature and subsequently is discharged onto an ice/water mixture. The cold sulfochloride suspension is filtered off with suction and washed with ice water until acid-free.

The moist sulfochloride paste thus obtained is suspended in 1,200 parts of ice/water, treated with 21 parts of cyanamide and held at pH 10 by means of sodium hydroxide solution. The reaction mixture is stirred at room temperature until the pH value remains constant without a further addition of sodium hydroxide solution.

The resulting solution is clarified by filtration, treated with 3 parts of zinc chloride, adjusted to pH 12 with sodium hydroxide solution and stirred at 40° to 45° C. for 2 hours. The solution is then adjusted to pH 1 with concentrated hydrochloric acid and evaporated to dryness. The residue is finely powdered and then stirred up for 1 hour in 500 parts of water. The suspension is filtered, and the material on the filter is washed with a little water. The residue is stirred up in 1,000 parts of water, the pH is adjusted to 7 with sodium hydroxide solution and the resulting solution is evaporated to dryness.

The compound thus obtained is of the formula

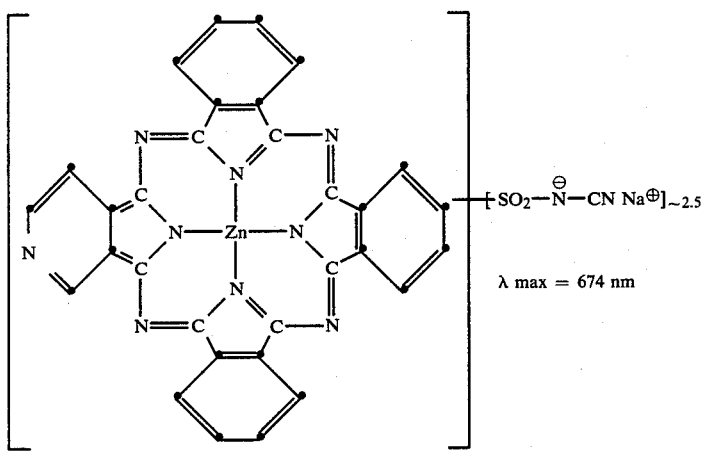

(915)

continuous agitation; "dyeing" is then carried out in the cooling liquor for a further 16 hours. 5 g of sodium chloride are then added to the tea liquor and treatment is carried out at 100° C. for a further 2 ½ hours. Finally, the liquor is cooled and the soiled cotton is rinsed twice at 60° C. and dried at 100° C. Finally, the soiled fabric is also washed for 20 minutes at 90° C. and at a liquor ratio of 1:20 with a liquor containing 5 g/l of detergent (see above for composition), subjected to a hot and cold rinse and dried at 100° C. in a circulating air oven.

** Lamp used: "Philips" infrared lamp (white) 220/230 V, 250 W, using a type 13372 E/06 reflector. The lamp is mounted approx. 25 cm above the wash liquor.

The piece of fabric is then rinsed and dried and subsequently assessed visually, in the course of which it is found that its brightness is far higher than that of the soiled fabric.

The degree of bleaching of the treated piece of fabric is also determined by measuring the whiteness (brightness value) Y (expressed as a percentage, based on absolute white as specified in the CIE Recommendation of 1.1.1969) by means of an ®Elrepho spectrophotometer made by ZEISS. The values determined confirm the visual impression and show that, as a result of adding the photosensitiser of the formula (401), a considerable gain in brightness ($\Delta Y$) is achieved, compared with the comparison fabric washed without a photosensitiser.

EXAMPLE 12

A cotton fabric weighing 1 g and soiled with tea* is treated at 40° C., while being exposed to a 250 W IR lamp** for one hour, with stirring, in 100 ml of an aqueous wash liquor containing 0.005%, based on the weight of the fabric, of the compound of the formula (401) and 0.5 g of a detergent of the following composition:
Sodium dodecylbenzenesulfonate: 16%
Sodium tripolyphosphate: 43%
Sodium silicate: 4%
Magnesium silicate: 2%
Fatty alcohol sulfate: 4%
Sodium carboxymethylcellulose: 1%
Sodium ethylenediaminetetraacetate: 0.5%
Sodium sulfate: 29.5%

* The cotton fabric is soiled with tea in the following manner:

15 g of tea ("Fine Ceylon Fannings Tea") are boiled for 1 hour in 600 ml of demineralised water, and the solution is then filtered. The tea leaves filtered off are taken up in 400 ml of demineralised water and boiled again for approx. 60 minutes. The two filtrates are combined and made up to 1000 ml with demineralised water. 45 g of cotton fabric (bleached and mercerised) are treated with this tea for 2 ½ hours at 100° C. and with

EXAMPLE 13

The procedure described in Example 12 is repeated, but a fabric soiled with red wine (EMPA test fabric No. 114, see Example 12), bilberry juice or cherry juice is employed instead of the test fabric soiled with tea. These test fabrics are also excellently bleached by means of the photoactivator of the formula (401), and a considerable gain in brightness compared with the comparison fabric washed without photoactivator is also achieved.

EXAMPLE 14

Each of 5 samples of 5 g of a cotton fabric dyed with a brown dye * is put into 500 ml of a wash liquor containing 5 g/l of a detergent of the composition indicated in Example 12 and also 0.005%, based on the weight of fabric, of the compound of the formula (401). The samples to be bleached are washed for 120 minutes at 50° C., with continuous agitation and while exposed to a lamp described in Example 12. The samples are then rinsed and dried, and the degree of bleaching of the dried samples is then measured in the form of brightness values, expressed as a percentage based on the absolute white as specified in the CIE Recommendation of 1.1.1969, by means of an ®Elrepho photometer made by ZEISS (standard illuminant D 65, 2 degrees standard observer, measuring diaphragm 35 mm $\phi$). The brightness values measured, which are far higher than those of the dyed fabric before and after washing in the absence of photoactivator, show that the soiled fabric is excellently bleached by means of the photoactivator employed.

* The cotton samples are dyed in the following manner:

150 mg of the commercially available brown dye of the formula

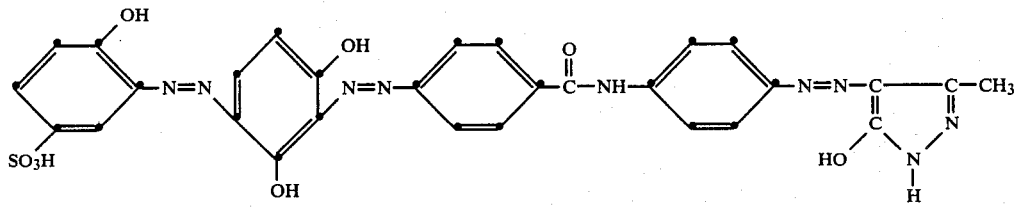

are dissolved, at a temperature of 50° C., in 2000 ml of water containing 1 g of sodium carbonate. 100 g of cotton fabric (bleached and mercerised) are dyed in this dye liquor with continuous agitation by heating the liquor to 90° C. in the course of 30 minutes. Dyeing is carried out at 90° C. for 90 minutes, during which time 20 g of sodium sulfate decahydrate are added in 4 portions of equal size at intervals of 15 minutes.

After dyeing, the cotton is subjected to 2 cold rinses and coppered for 20 minutes at 60° C. and at a liquor ratio of 1:20 in a liquor containing 0.75 g/l of crystalline copper sulfate and 1 ml/l of glacial acetic acid. The dyeing is then subjected to 2 cold rinses and dried at 100° C. in a hot air oven.

EXAMPLE 15

10 g portions of a test fabric (EMPA test fabric No. 114, obtainable at the Eidgenössische Materialprüfund Versuchsanstalt ("Federal Institution for Materials Testing and Research"), CH-9001 St. Gallen, Unterstrasse 11) which has been soiled with red wine are washed for 30 minutes at 50° C. and at a liquor ratio of 1:50 in wash liquors containing the following ingredients:

Liquor 1: 4 g/l of the detergent of the composition indicated in Example 12,
Liquor 2: 4 g/l of the detergent of the composition indicated in Example 12, 0.0005 g of the compound of the formula (401)
Liquor 3: 4 g/l of the detergent of the composition indicated in Example 12, 1 g/l of sodium perborate and 0.5 g/l of tetraacetylethylenediamine (bleach activator)
Liquor 4: 4 g/l of the detergent of the composition indicated in Example 12, 1 g/l of sodium perborate, 0.5 g/l of tetraacetylethylenediamine and 0.0005 g of the compound of the formula (401).

After being washed, the pieces of fabric are subjected to a brief rinse and are then laid in the sun for 2 hours and moistened several times. The degree of bleaching (the brightness) of the fabric samples is then determined as indicated in Example 12 or 14.

The results obtained show that the fabric samples washed in liquor 2 have appreciably higher brightness values than those washed in liquor 1. The comparison of the washing tests in liquors 3 and 4 shows that the addition of a photoactivator (in this case of the formula (401)) to an activated perborate bleach liquor is capable of causing an additional considerable increase in the brightness of the washed pieces of fabric. The fabric samples washed in liquor 4 are distinctly brighter than those washed in liquor 3.

EXAMPLE 16

A washing agent slurry, consisting of 50 parts of deionised water and 50 parts of a washing agent of the following composition, is prepared:

8.0% of linear sodium alkylbenzenesulfonate (chain length of the alkyl ester: $C_{11.5}$), 2.9% of tallow alcohol tetradeka-ethylene glycol ether (14 EO), 3.5% of sodium soap (chain lengths $C_{12-16}$: 13–26%; $C_{18}$–$C_{22}$: 74–87%), 43.8% of sodium triphosphate, 7.5% of sodium silicate ($SiO_2$: $Na_2O = 3.3:1$), 1.9% of magnesium silicate, 1.2% of carboxymethylcellulose, 0.2% of Na ethylenediaminetetraacetate, 21.2% of sodium sulfate, 0.03% of photoactivator of the formula (401), 0.13% of 4,4'-bis-(2-sulfostyryl)-biphenyl Na salt (fluorescent brightener) and water to make up to 100%.

The photoactivator and the brightener are added with substantial exclusion of light to the washing agent slurry defined above, but not yet containing these two components, and the mixture is dried for 4 hours in a drying box under a vacuum of approx. 400 mmHg and at 80° C. The resulting encrustations of washing agent are forced through a sieve under which another sieve is located, so that a washing powder of uniform particle size is produced.

The test substrates used are strips of bleached cotton fabric which have been soiled by fruit juices (cherry, elderberry, blackberry, red currant and bilberry juice), tea (see Example 12), blood (EMPA test fabric, type 103, series 23) or red wine (EMPA test fabric No. 114).

Test strips from each of the soiled fabrics just described are washed for 30 minutes at 50° C. and at a liquor ratio of 1:20 in a liquor containing 4 g per liter of the washing agent defined above, and are then subjected to a brief rinse and hung, moist after spinning, on a line in daylight and left to dry for 6 hours, being sprayed every 40 minutes with an alkaline solution of pH 9. These washing tests are also carried out with a washing agent containing no fluorescent brightener or no photoactivator or none of either. The degree of soil removal is assessed visually. A rather modest removal of soil is obtained when the washing agent with no fluorescent brightener or photoactivator is used. Very good and pronounced bleaching effects are achieved in the presence of the photoactivator (without fluorescent brightener). When the fluorescent brightener (but no photoactivator) is present, bleaching effects are obtained which are, however, less than when the photoactivator is present alone. By far the best results in all types of soiling are achieved when photoactivator and fluorescent brightener are present. In each case an extremely bright and strongly bleached cotton fabric results.

The effects obtained on a standardised piece of cotton dyed brown (see Example 14) are evaluated colorimetrically. This fully confirms the results obtained visually.

Entirely analogous results are obtained if 4,4'-bis(4-phenyl-1,2,3-triazol-2-yl)-2,2'-stilbenedisulfonic acid (K salt) is employed as the fluorescent brightener in the washing agent of the composition described above.

EXAMPLE 17

100 parts of a stock washing agent of the composition indicated in Example 12 are made into a slurry with 50 ml of water. 0.02 part of the photoactivator of the formula (401) and 0.15 part of 4,4'-bis-(2-sulfostyryl)-biphenyl Na salt (fluorescent brightener) are dissolved in a little water, which is added to the washing agent slurry and thoroughly mixed with it. The slurry is dried at 105° C. in a drying cabinet, pulverised and processed as described in Example 16 to give a washing powder of uniform particle size.

A cotton fabric weighing 5 g and dyed with a brown dye in accordance with Example 14 is treated for 30 minutes at 35° C. with 100 ml of a wash liquor containing 0.5 g of the washing powder obtained as described above. Without rinsing, the fabric is then laid on a filter paper impregnated with the wash liquor and irradiated for 90 minutes with a 250 W IR lamp (as described in Example 12; distance of the lamp from the fabric: approx. 30 cm). The fabric is then rinsed and dried, and the degree of bleaching (increase in brightness) is determined as described in Example 12. The whole process (washing, exposure to light and determination of brightness) is repeated five times. Result: up to the 5th cycle, the brightness value of the fabric increases continuously without a tendency to greenish discoloration being discernible.

EXAMPLE 18

Comparable bleaching effects are obtained if a photoactivator of the formula (402) to (404) or (601) to (604) is employed in Examples 12–17 instead of the photoactivator of the formula (401).

EXAMPLE 19

Test of activity against bacteria

Method: A microbial suspension of Staphylococcus aureus ATCC 6538 having a defined amount of microbes per ml is added to an aqueous solution containing one of the compounds of the formulae (401) to (404) or (601) to (604) in concentrations of 0.01, 0.1 and 1.0 ppm. This test suspension is in a beaker under a water-cooled sheet of glass in order to prevent heating caused by the subsequent exposure to light. Irradiation is then carried out for 5, 10, 20, 30 and 60 minutes by means of an incandescent lamp or an infrared lamp (Philips IR, 250 W, type 13372 E/06 "Weiss" ("white") infrared lamp), located at a distance of 20 cm above the surface of the suspension. The microbial count is then determined in the customary manner by parallel counting. The reduction in microbes in a particular case is calculated in powers of ten in accordance with the formula $x = -\log_{10} N/N_o$, where $N_o$ is the microbial inoculation and N is the number of microbes surviving.

The results show that the compounds tested reduce the number of test microbes by 2 to 6 powers of ten, depending on the concentration employed and the duration of exposure to light.

EXAMPLE 20

Test of the disinfecting action on textiles

A piece of cotton fabric is clamped on a metal grid and inoculated with a test suspension (containing one of the compounds of the formulae (401) to (404) or (601) to (604) and a test microbe strain) described in Example 19. The metal grid, which is connected to a motor, is then rotated and irradiated with an infrared lamp. A sheet of glass cooled with running water is placed between the lamp and the piece of fabric, in order to prevent the piece of fabric from being heated. Parallel to this, a piece of fabric is treated under identical test conditions, but with no antimicrobial active substance applied to it. After exposure for 1 hour, the microbial counts are measured quantitatively and the reduction in microbes effected by the particular azaphthalocyanine is determined. The action against Staphylococcus aureus ATCC 6538 is tested. Reductions in microbes similar to those in Example 19 are found.

EXAMPLE 21

Surface disinfection

Enamelled floor tiles of dimensions 4×4 cm are inoculated with a microbial suspension of Staphylococcus aureus ATCC 6538; approx. 10⁵ microbes are thereby distributed uniformly over the surface of a floor tile. An aqueous solution containing 1 ppm of one of the compounds of the formulae (401) to (404) or (601) to (604) is then sprayed on to the surface. The surface is then irradiated for 30 or 45 minutes with an incandescent lamp (250 W, distance: 20 cm) Samples are taken after this time by transfer into Rodac dishes. No further microbial growth can be observed after 45 minutes treatment with the said compounds.

EXAMPLE 22

Sterilising a sewage treatment plant effluent

A sample of sludge is taken from a laboratory sewage treatment apparatus and is filtered through a paper filter. One of each of the azaphthalocyanine compounds to be tested, of the formulae (401) to (404) or (601) to (604), is added to the filtrate, which contains approx. $10^6$ microbes/ml, to give a concentration of 1 ppm of the compound in the filtrate. The latter is then illuminated with standard light, 380–730 nm, at 300 mW/cm². The number of germs surviving is determined after varying intervals of time. Even after 45 minutes, no more Staphylococci are present. The number of other microbes present in the filtrate also decreases markedly after a longer period of exposure (1 or more hours).

EXAMPLE 23

Sterilising swimming pools

Swimming pools containing 5,000 l of water apiece are installed in the open. The water in each pool is treated with one of the compounds of the formulae (401) to (404) or (601) to (604), in a concentration of 0.5 ppm. Samples of water are taken at intervals of 1–5 days, and the microbial counts are determined quantitatively. The microbiological testing determines a) the total microbial count and b) the number of coliform microbes.

Result: In the pool containing none of the azaphthalocyanine compounds tested, the coliform microbes multiply to $2-3\times 10^1$ microbes/100 ml. In a pool containing an active substance, no coliform microbes are detected up to the 16th day of the test.

For a further test, a microbial suspension containing *Staphylococcus aureus* ATCC 6538 and *Escherichia coli* ATCC 11229 is added to the water in an amount of 50 microbes per 100 ml of pool content in each case, on the 16th day of the test. A measurement immediately after the introduction of the microbes shows a uniform distribution in the pool. After 24 hours, no coliform microbes nor any Staphylococci are detected in the pool containing the active substance (100 ml of water taken in each case). The total microbial count, consisting of autochthonous microbial flora (native to the swimming pool) remained constant during the period of the test.

What we claim is:

1. A process for carrying out a reaction with singlet oxygen, which comprises bringing a compound of the formula

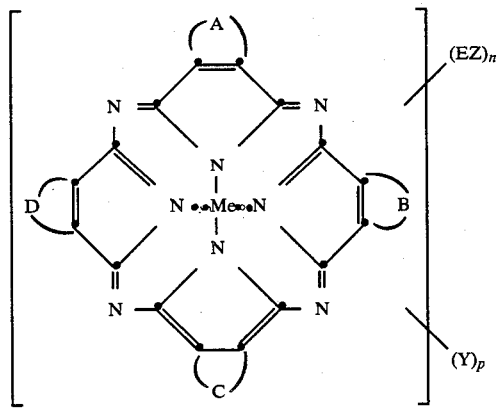

in which Me is Al(III), Zn(II), Ge(IV) or Sn(IV), E is a sulfo, carboxyl, phosphate, sulfate, sulfinyl, disulfimide or sulfocyanimide group or a radical containing one or more of the above mentioned groups, Z is a cation, Y is halogen, n is a 1 to 3 and p is a 0 to 2, the sum n+p being at most 8 and A, B, C and D independently of one another completing a benzene ring or a ring of the formula

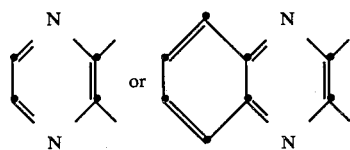

at leat one of the rings completed by A, B, C, or D being one of the said heterocyclic rIngs into contact with a substrate in the presence of oxygen and water and irradiating with light.

2. A process for carrying out a reaction with singlet oxygen, which comprises bringing one or more compounds of the formula

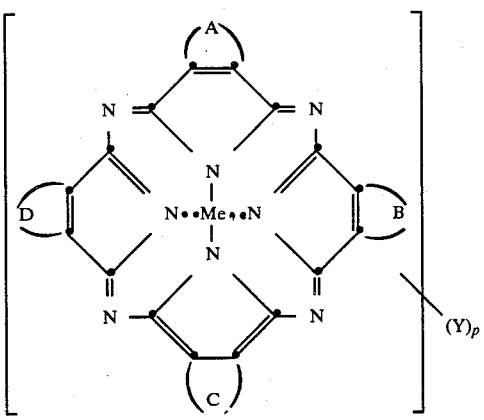

in which Me is Al(III), Zn(II), Ge(IV) or Sn(IV), A, B, C and D independently of one another complete a benzene ring or a ring of the formula

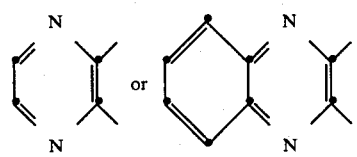

at least one of the rings completed by A, B, C and D being one of the said heterocyclic rings, Y is a halogen and p is any desired number from 0 to 2, with the proviso that Me is other than Zn(II) if A, B, C and D are identical and complete one of the said heterocyclic rings and simultaneously p is 0, into contact with a substrate in the presence of oxygen and water, and irradiating with light.

3. A composition containing as a singlet oxygen producing compound a compound of the formula

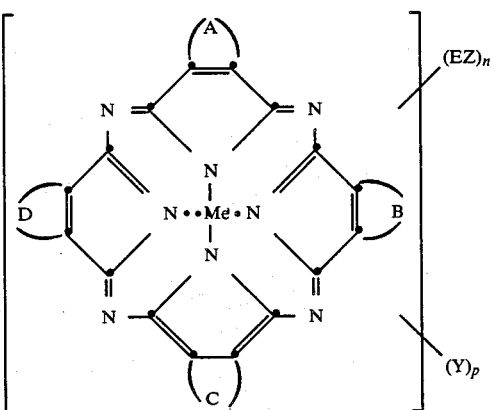

in which Me is Al(III), Zn(II), Ge(IV) or Sn(IV), E is a sulfo, carboxyl, phosphate, sulfate, sulfinyl, disulfimide or sulfocyanimide group or a radical containing one or more of the above mentioned groups, Z is a cation, Y is a halogen, n is a 1 to 3 and p is a 0 to 2, the sum n+p being at most 8 and A, B, C and D independently of one another completing a benzene ring or a ring of the formula

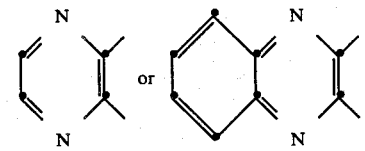

at least one of the rings completed by A, B, C or D being one of said heterocyclic rings.

4. A composition according to claim 3, which contains 0.0005 to 1.5 per cent by weight, relative to the total composition, a compound according to claim 19.

* * * * *